(12) United States Patent
Gross

(10) Patent No.: US 11,395,910 B2
(45) Date of Patent: Jul. 26, 2022

(54) PASSIVE PUMP

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 0 days.

(21) Appl. No.: 17/524,225

(22) Filed: Nov. 11, 2021

(65) Prior Publication Data

US 2022/0062619 A1 Mar. 3, 2022

Related U.S. Application Data

(63) Continuation-in-part of application No. PCT/IL2021/050567, filed on May 18, 2021, and a
(Continued)

(51) Int. Cl.
*A61M 60/869* (2021.01)
*A61M 60/17* (2021.01)
(Continued)

(52) U.S. Cl.
CPC ........ *A61M 60/869* (2021.01); *A61M 60/135* (2021.01); *A61M 60/17* (2021.01);
(Continued)

(58) Field of Classification Search
CPC .. A61M 60/869; A61M 60/135; A61M 60/17; A61M 60/295; A61M 60/843; A61M 60/865
See application file for complete search history.

(56) References Cited

U.S. PATENT DOCUMENTS

| 4,546,759 A | 10/1985 | Solar |
| 4,994,017 A | 2/1991 | Yozu |

(Continued)

FOREIGN PATENT DOCUMENTS

| WO | 2004/066805 | 8/2004 |
| WO | 2004/108191 | 12/2004 |

(Continued)

OTHER PUBLICATIONS

An International Search Report and a Written Opinion both dated Apr. 15, 2016, which issued during the prosecution of Applicant's PCT/IL2016/050050.
(Continued)

*Primary Examiner* — Amanda K Hulbert
*Assistant Examiner* — Natasha Patel
(74) *Attorney, Agent, or Firm* — Sughrue Mion, PLLC

(57) ABSTRACT

A method for repairing a heart includes identifying a heart of a patient as having a reduced ejection fraction. In response to the identifying, wall stress of a ventricle of the heart is reduced by implanting apparatus that facilitates cyclical moving of fluid that is not blood of the patient into and out of the ventricle of the heart. During ventricular diastole, a volume of the fluid is moved into the ventricle in a manner that produces a corresponding decrease in a total volume of blood that fills the ventricle during diastole. During ventricular systole, the volume of the fluid is moved out of the ventricle in a manner that produces a corresponding decrease in a total volume of the ventricle during isovolumetric contraction of the ventricle. Other embodiments are also described.

25 Claims, 17 Drawing Sheets

STAGE A

Related U.S. Application Data continuation-in-part of application No. 16/879,164, filed on May 20, 2020, now Pat. No. 11,219,754.

(51) Int. Cl.
- *A61M 60/135* (2021.01)
- *A61M 60/843* (2021.01)
- *A61M 60/865* (2021.01)
- *A61M 60/295* (2021.01)

(52) U.S. Cl.
CPC ........ *A61M 60/295* (2021.01); *A61M 60/843* (2021.01); *A61M 60/865* (2021.01)

(56) References Cited

U.S. PATENT DOCUMENTS

| | | | |
|---|---|---|---|
| 4,994,078 | A | 2/1991 | Jarvik |
| 5,139,517 | A | 8/1992 | Corral |
| 5,192,314 | A * | 3/1993 | Daskalakis ...... A61B 17/12136 623/3.21 |
| 5,762,599 | A | 6/1998 | Sohn |
| 5,810,757 | A | 9/1998 | Sweezer, Jr. et al. |
| 5,891,012 | A | 4/1999 | Downey et al. |
| 6,332,893 | B1 | 12/2001 | Mortier et al. |
| 6,406,422 | B1 * | 6/2002 | Landesberg ........ A61M 60/135 600/17 |
| 6,432,039 | B1 | 8/2002 | Wardle |
| 6,511,413 | B2 | 1/2003 | Landesberg |
| 6,673,043 | B1 | 1/2004 | Landesberg |
| 7,159,593 | B2 | 1/2007 | McCarthy et al. |
| 7,404,824 | B1 | 7/2008 | Webler et al. |
| 7,431,692 | B2 | 10/2008 | Zollinger et al. |
| 7,476,200 | B2 | 1/2009 | Tal |
| 7,483,743 | B2 | 1/2009 | Mann et al. |
| 7,635,329 | B2 | 12/2009 | Goldfarb et al. |
| 7,862,501 | B2 | 1/2011 | Woodard |
| 7,927,268 | B1 | 4/2011 | St Germain et al. |
| 8,057,493 | B2 | 11/2011 | Goldfarb et al. |
| 8,147,542 | B2 | 4/2012 | Maisano et al. |
| 8,475,525 | B2 | 7/2013 | Maisano et al. |
| 8,790,394 | B2 | 7/2014 | Miller et al. |
| 8,876,850 | B1 | 11/2014 | Vollmers et al. |
| 8,961,596 | B2 | 2/2015 | Maisano et al. |
| 9,232,999 | B2 | 1/2016 | Maurer et al. |
| 9,517,129 | B2 | 12/2016 | Wilson et al. |
| 9,545,305 | B2 | 1/2017 | Wilson et al. |
| 9,833,316 | B2 | 12/2017 | Wilson et al. |
| 10,039,643 | B2 | 8/2018 | Gilmore et al. |
| 10,039,874 | B2 | 8/2018 | Schwammenthal et al. |
| 10,098,992 | B2 | 10/2018 | Van Dort et al. |
| 10,286,131 | B2 | 5/2019 | Sohn et al. |
| 10,405,978 | B2 | 9/2019 | Maisano et al. |
| 10,517,719 | B2 | 12/2019 | Miller et al. |
| 10,610,360 | B2 | 4/2020 | Reich et al. |
| 10,722,631 | B2 | 7/2020 | Salahieh et al. |
| 10,751,184 | B2 | 8/2020 | Reich et al. |
| 10,820,998 | B2 | 11/2020 | Marr et al. |
| 10,888,644 | B2 | 1/2021 | Ratz et al. |
| 10,973,966 | B2 | 4/2021 | Sohn et al. |
| 11,051,940 | B2 | 7/2021 | Metchik et al. |
| 2002/0169360 | A1 | 11/2002 | Taylor et al. |
| 2002/0173693 | A1 | 11/2002 | Landesberg |
| 2002/0173742 | A1 | 11/2002 | Keren et al. |
| 2003/0216801 | A1 | 11/2003 | Tweden et al. |
| 2004/0111006 | A1 | 6/2004 | Alferness et al. |
| 2005/0148925 | A1 | 7/2005 | Rottenberg et al. |
| 2005/0154250 | A1 | 7/2005 | Aboul-hosn et al. |
| 2005/0165344 | A1 | 7/2005 | Dobak, III |
| 2005/0256566 | A1 | 11/2005 | Gabbay |
| 2006/0064059 | A1 | 3/2006 | Gelfand et al. |
| 2006/0206029 | A1 | 9/2006 | Tal |
| 2006/0241745 | A1 | 10/2006 | Solem |
| 2007/0073218 | A1 | 3/2007 | Lau et al. |
| 2007/0299296 | A1 | 12/2007 | Vaska |
| 2008/0004485 | A1 | 1/2008 | Moreschi |
| 2008/0207986 | A1 | 8/2008 | Choy |
| 2010/0023117 | A1 | 1/2010 | Yoganathan et al. |
| 2010/0057192 | A1 | 3/2010 | Celermajer |
| 2010/0298929 | A1 | 11/2010 | Thornton et al. |
| 2011/0112632 | A1 | 5/2011 | Chau et al. |
| 2011/0218480 | A1 | 9/2011 | Rottenberg et al. |
| 2011/0306916 | A1 | 12/2011 | Nitzan et al. |
| 2012/0059213 | A1 | 3/2012 | Spence |
| 2012/0143320 | A1 | 6/2012 | Eliasen et al. |
| 2014/0135567 | A1 * | 5/2014 | Marotta ............... A61M 60/17 600/17 |
| 2014/0213959 | A1 | 7/2014 | Nitzan et al. |
| 2015/0335801 | A1 | 11/2015 | Farnan et al. |
| 2016/0015877 | A1 | 1/2016 | Guerrero et al. |
| 2016/0166747 | A1 | 6/2016 | Frazier et al. |
| 2017/0136162 | A1 | 5/2017 | Van Dort et al. |
| 2017/0231766 | A1 | 8/2017 | Hariton et al. |
| 2017/0325949 | A1 | 11/2017 | Rodgers et al. |
| 2018/0001004 | A1 | 1/2018 | Sohn et al. |
| 2020/0188101 | A1 | 6/2020 | Chambers |
| 2021/0022858 | A1 | 1/2021 | Miller et al. |
| 2021/0121679 | A1 | 4/2021 | Mohl et al. |
| 2021/0177425 | A1 * | 6/2021 | Kapur .............. A61B 17/12045 |
| 2021/0361839 | A1 | 11/2021 | Gross |
| 2021/0379354 | A1 * | 12/2021 | Tansley ................ A61M 60/17 |

FOREIGN PATENT DOCUMENTS

| | | |
|---|---|---|
| WO | 2007/132449 | 11/2007 |
| WO | 2007/149562 | 12/2007 |
| WO | 08/141325 | 11/2008 |
| WO | 2010/128501 | 11/2010 |
| WO | 2014/203078 | 12/2014 |
| WO | 2015/177793 | 11/2015 |
| WO | 2016/113743 | 7/2016 |
| WO | 2020/081481 | 4/2020 |
| WO | 2021/234691 | 11/2021 |

OTHER PUBLICATIONS

Notice of Allowance dated Jul. 8, 2021, which issued during the prosecution of U.S. Appl. No. 16/879,164.
Notice of Allowance dated Sep. 22, 2021, which issued during the prosecution of U.S. Appl. No. 16/879,164.
Matheus Pessanha de RezendeI et al. "Carbon dioxied use as contrast for vena cava filter implantation: case seriess" Jornal Vascular Brasileiro Print version ISSN 1677-5449 J. vasc. bras. vol. 11 No. 1 Porto Alegre Mar. 2012 https://doi.org/10.1590/S1677-54492012000100004.
Notice of Allowance dated Jun. 17, 2021, which issued during the prosecution of U.S. Appl. No. 16/879,164.
An Office dated Dec. 7, 2020, which issued during the prosecution of U.S. Appl. No. 16/879,164.
An Office Action dated Feb. 2, 2021, which issued during the prosecition of U.S. Appl. No. 16/879,164.
An International Preliminary Report on Patentability dated Jul. 18, 2017, which issued during the prosecution of Applicant's PCT/IL2016/050050.
Notice of Allowance dated Jan. 4, 2019, which issued during the prosecution of U.S. Appl. No. 15/543,789.
An International Search Report and a Written Opinion both dated Aug. 23, 2021, which issued during the prosecution of Applicant's PCT/IL2021/050567.
Généreux, Philippe—AltaValve—CRT19 Mar. 2019 Presentation.
Carlsson M et al., "Atrioventricular plane displacement is the major contributor to left ventricular pumping in healthy adults, athletes, and patients with dilated cardiomyopathy," Am J Physiol Heart Circ Physiol 292: H1452-H1459, 2007.
U.S. Appl. No. 62/103,937, filed Jan. 15, 2015.

* cited by examiner

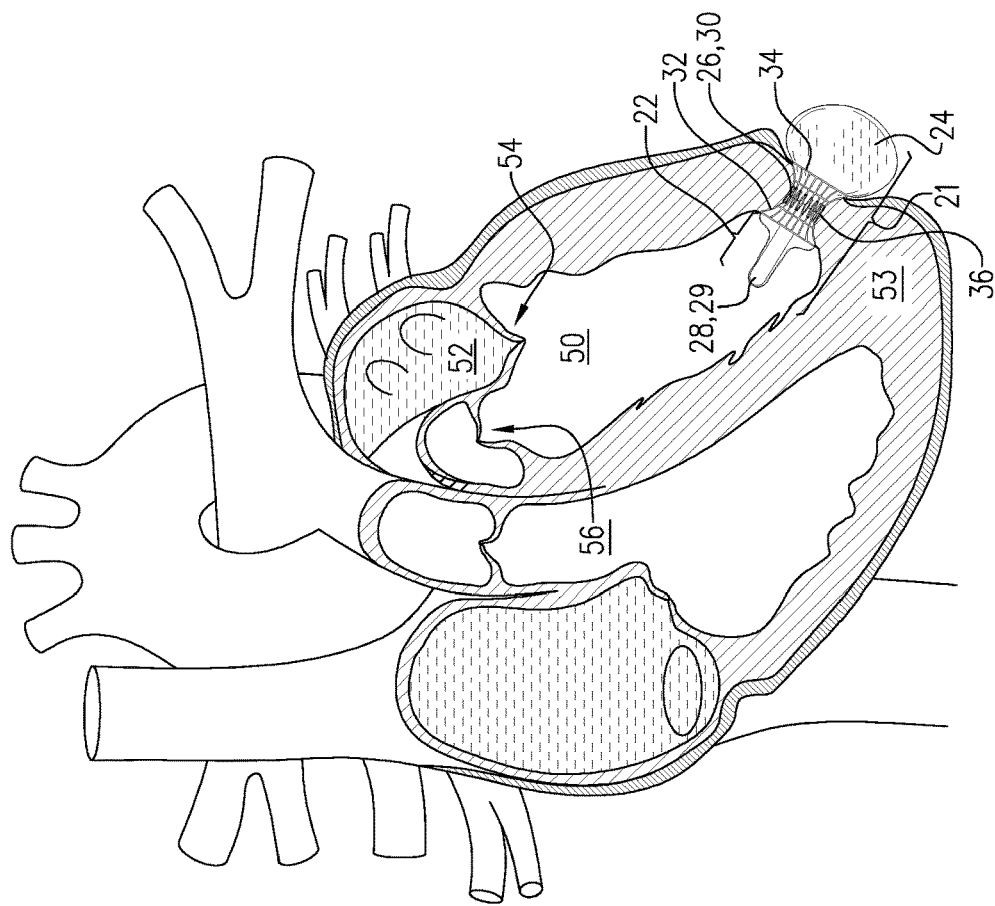
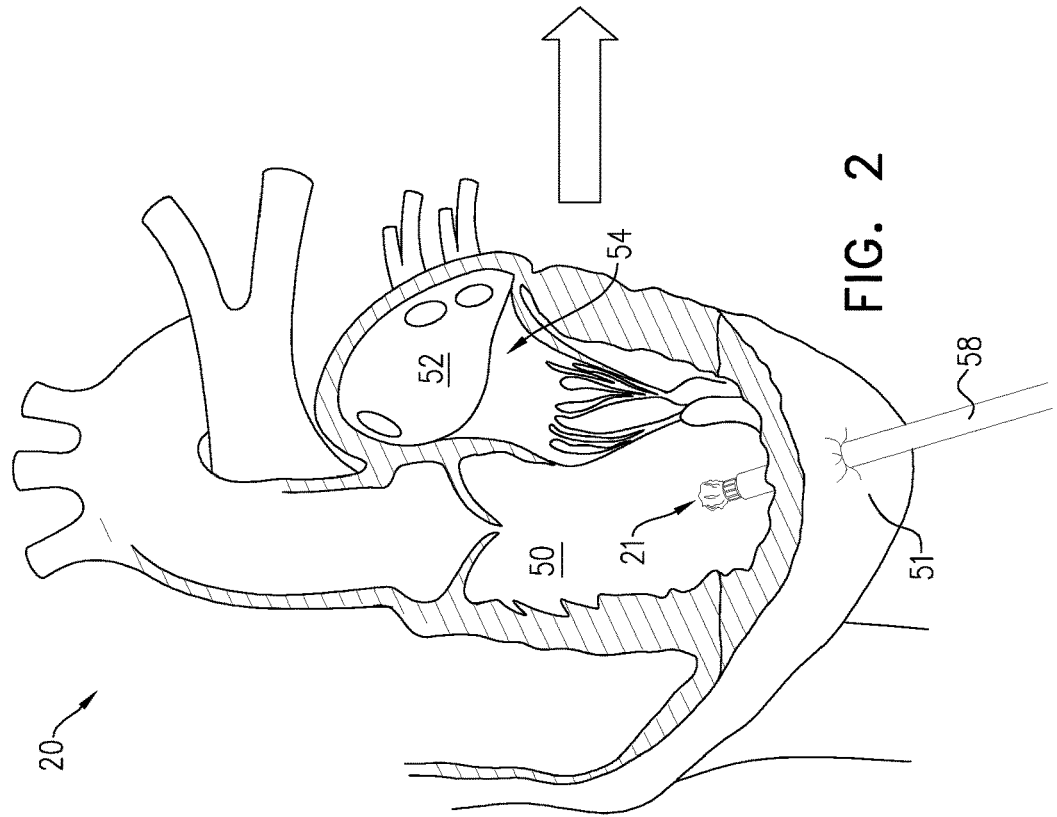
FIG. 2

STAGE A

STAGE B

STAGE C

STAGE D

STAGE F

STAGE E

STAGE G

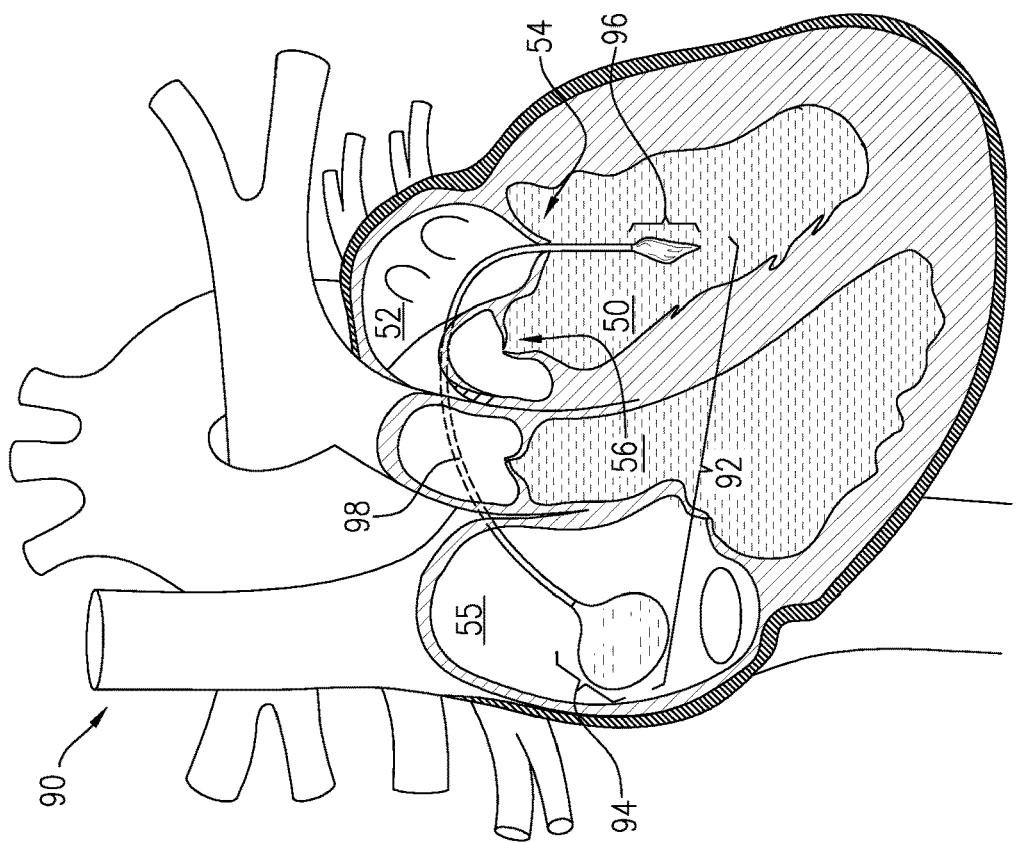
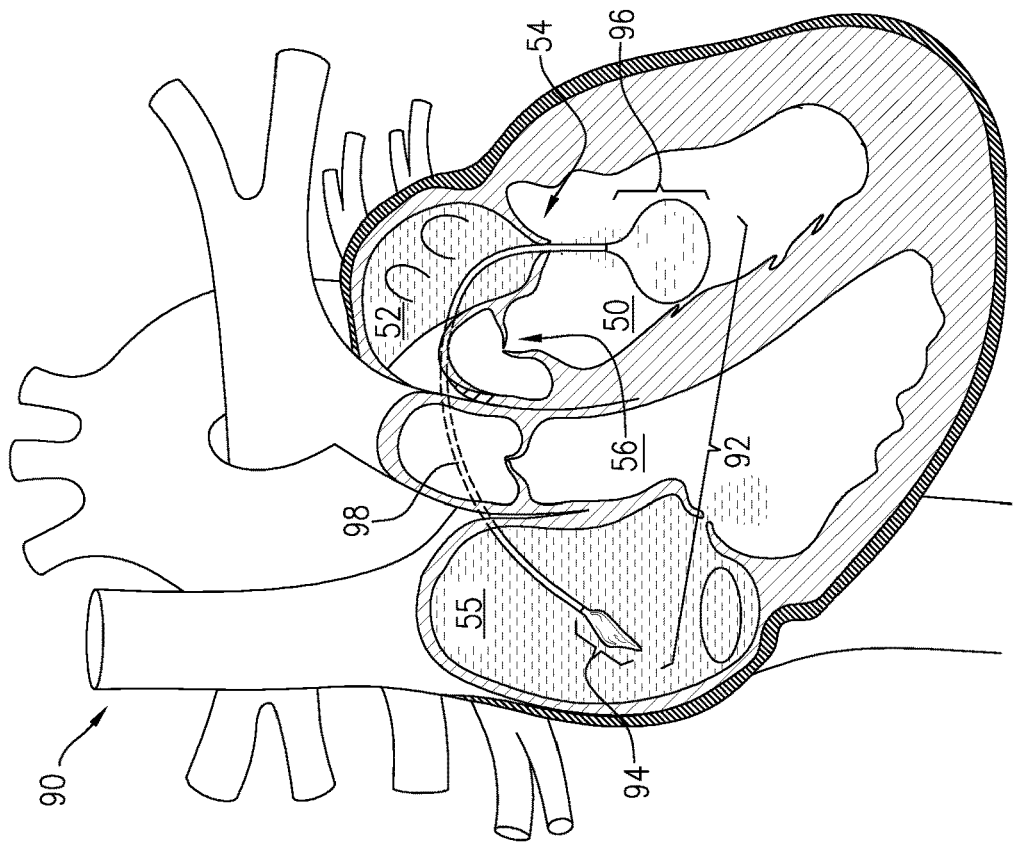
FIG. 7A
STAGE B
FIG. 7B
STAGE E

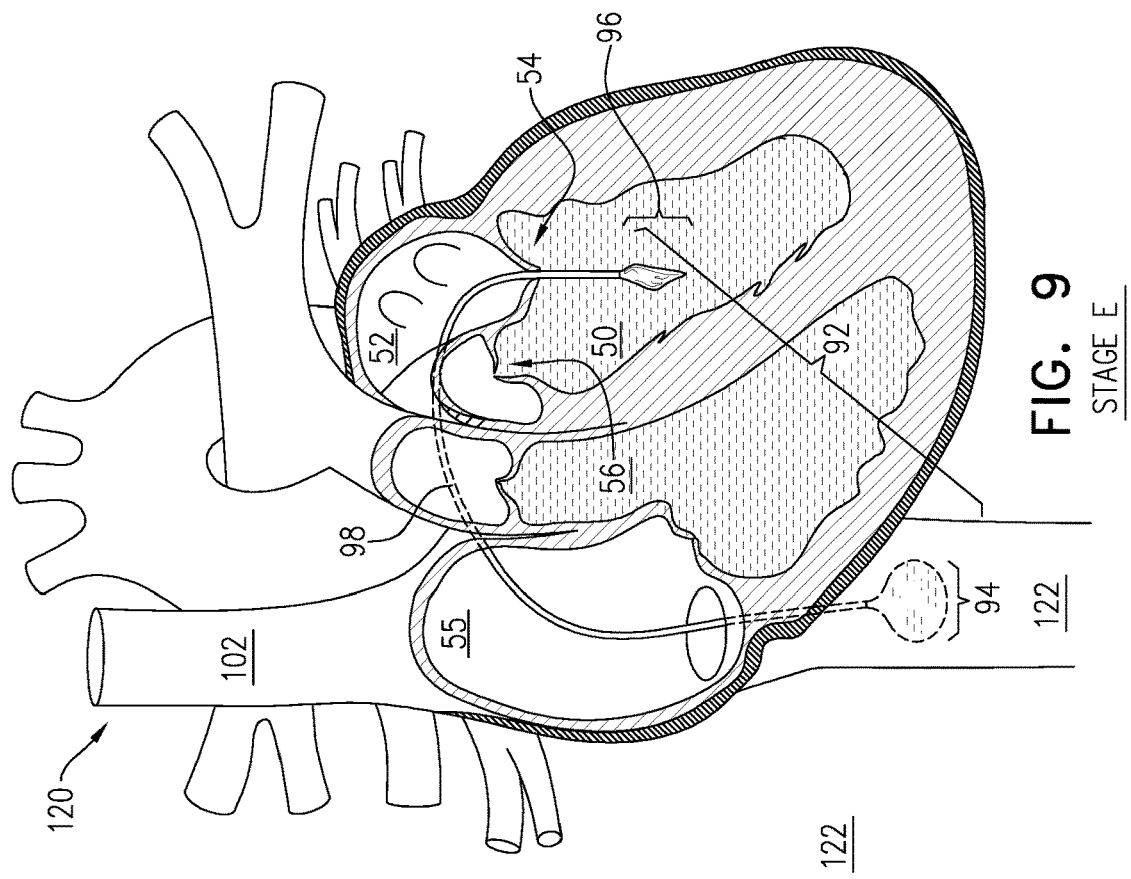
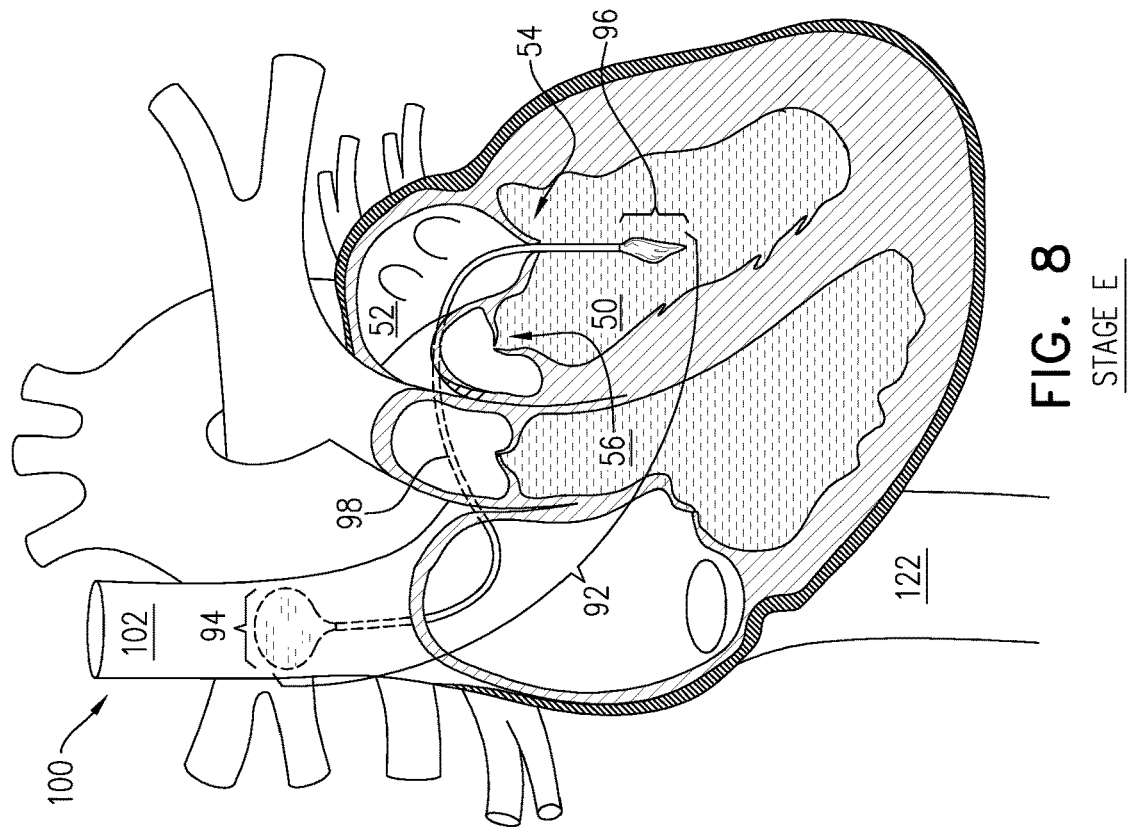

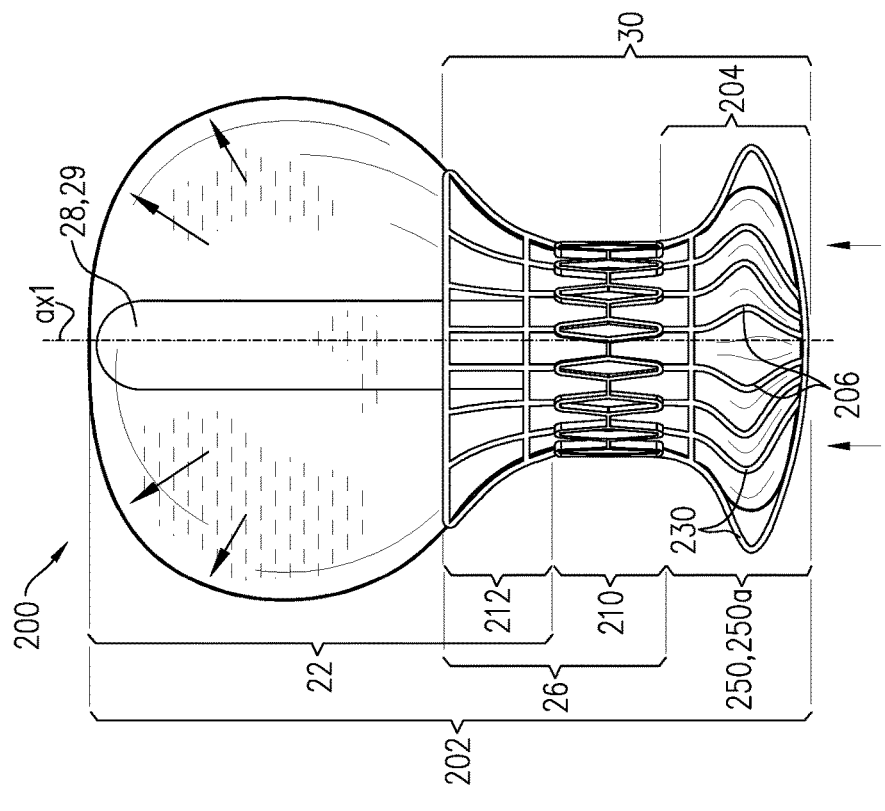
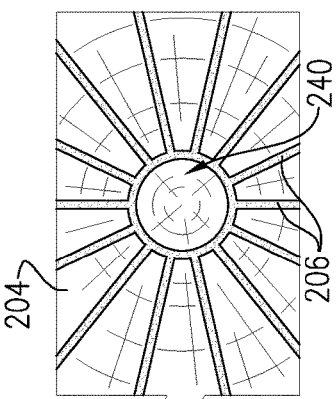
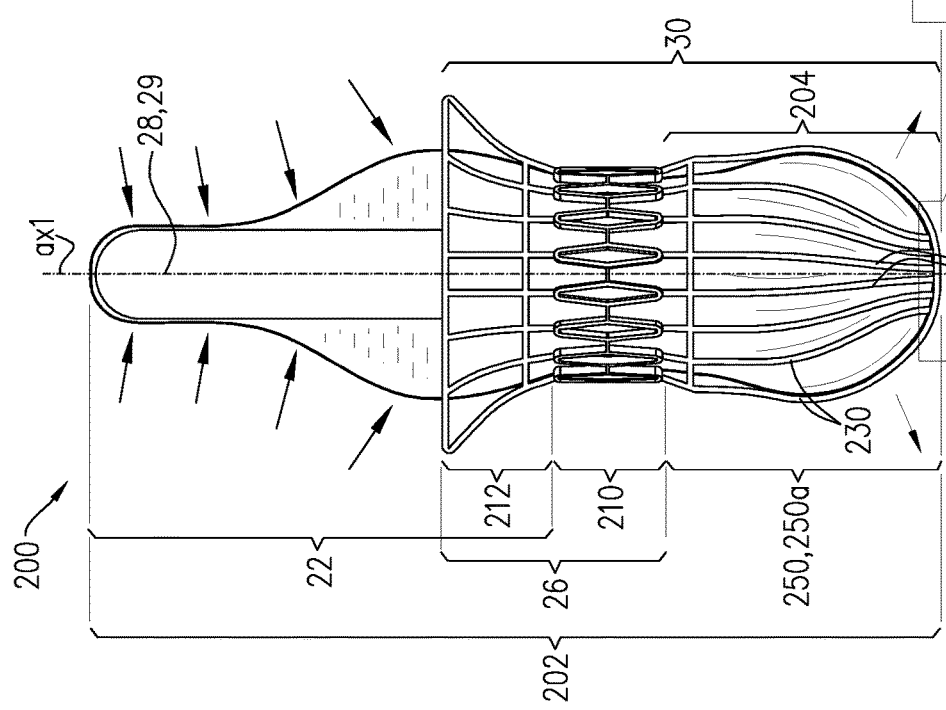
FIG. 12B
FIG. 12A

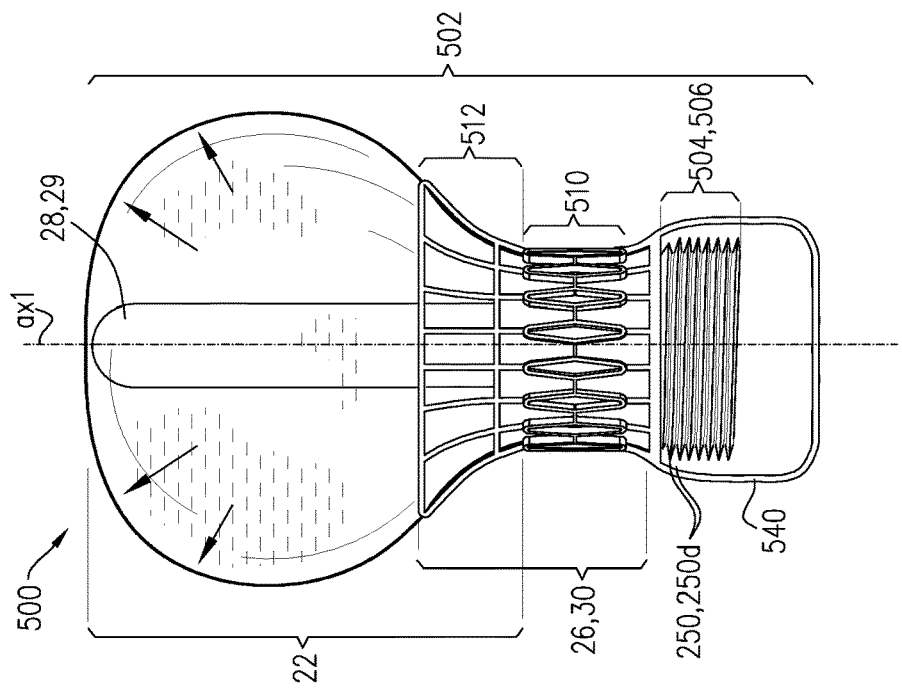
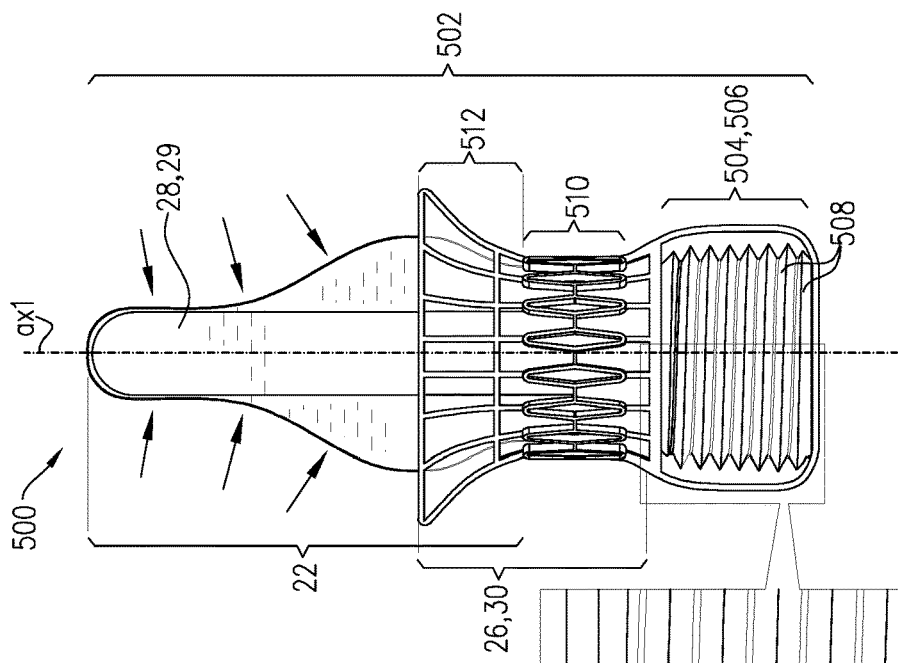
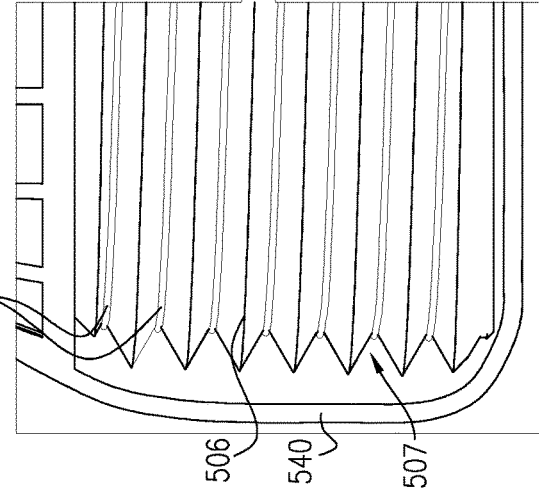
FIG. 15A
FIG. 15B

PASSIVE PUMP

CROSS-REFERENCE TO RELATED APPLICATIONS

The present application is a continuation-in-part application of:

U.S. patent application Ser. No. 16/879,164 to Gross, filed May 20, 2020, entitled, "Passive pump," and PCT Patent Application PCT/IL2021/050567 to Gross, filed May 18, 2021, entitled, "Passive pump," which claims the priority from and is a continuation application of U.S. patent application Ser. No. 16/879,164 to Gross, filed May 20, 2020, entitled, "Passive pump."

Each of these applications is incorporated herein by reference.

FIELD OF THE INVENTION

The present invention relates in general to heart repair. More specifically, the present invention relates to a method of repairing a failing heart utilizing a passive device which assists a ventricle of the heart.

BACKGROUND OF THE INVENTION

Heart failure is a condition in which the heart cannot pump enough blood to meet the body's needs. In some cases, the heart cannot fill with enough blood. In other cases, the heart cannot pump blood to the rest of the body with enough force.

Heart failure develops over time as the heart's pumping action grows weaker. The condition can affect one or both sides of the heart.

Systolic heart failure occurs when the contraction of the muscle wall of the left ventricle malfunctions, which compromises its pumping action. This causes a decrease in the ejection fraction below the normal range, and gradually, left ventricular remodeling occurs in the cardiac tissue which causes enlargement of the ventricle. The remodeling manifests as gradual increases in left ventricular end-diastolic and end-systolic volumes, wall thinning, and a change in chamber geometry to a more spherical, less elongated shape. This process is usually associated with a continuous decline in ejection fraction. In general, left-sided heart failure leaves the heart unable to pump enough blood into the circulation to meet the body's demands, and increasing pressure within the heart causes blood to back up in the pulmonary circulation, producing congestion.

SUMMARY OF THE INVENTION

In some applications of the present invention, apparatus is provided that is implantable at a heart of a patient and facilitates cyclical moving of fluid that is not blood of the patient into and out of a ventricle of the heart. That is, during ventricular diastole, a volume of the fluid is moved into the ventricle in a manner that produces a corresponding decrease in a total volume of blood that fills the ventricle during diastole. During ventricular systole, the volume of the fluid is moved out of the heart in a manner that produces a corresponding decrease in a total volume of the ventricle during isovolumetric contraction of the ventricle. In such a manner, the pressure rise in the ventricle occurs at a lower volume than the pressure rise would otherwise occur in a heart of a healthy subject. Typically, the fluid in the passive pump is moved between components of the passive pump responsively to pressure increases and decreases associated with stages of the cardiac cycle. Therefore, the pump is considered passive. The passive pump is typically not operably connected to machinery or circuitry which helps facilitate movement of the fluid between the components of the pump.

The apparatus typically comprises (a) a bag that is noncompliant, (b) a compliant balloon, (c) a conduit disposed between and in fluid communication with the bag and the compliant balloon, and (d) a volume of fluid disposed within an inner space defined by the apparatus. The volume of fluid is passable between the bag and the compliant balloon via the conduit passively and responsively to changes in pressure associated with respective stages of the cardiac cycle.

Except where indicated to the contrary, applications of the present invention described as utilizing a "fluid" may be implemented using either a liquid or a gas.

For some applications of the present invention, the apparatus comprises a second bag that is noncompliant, instead of the compliant balloon. In this case, a spring is typically, but not necessarily, coupled to the second bag to facilitate ejecting of the fluid from within the second bag.

Typically, the bag is positionable within the ventricle (e.g., the left ventricle or the right ventricle), and the compliant balloon, or second bag, is positionable outside the ventricle (e.g., in the right atrium, in the superior vena cava, in the inferior vena cava, or any suitable place outside of the heart).

For some applications, the bag is positionable within the ventricle, the compliant balloon is positionable outside of the heart, and the conduit is disposed transmyocardially. The compliant balloon is configured to expand upon transfer of the fluid into the balloon from the bag, and to contract upon passage of at least part of the fluid out of the balloon. During ventricular diastole, the balloon contracts and expels the fluid, through the conduit, into the bag within the ventricle. During ventricular systole, while the aortic valve of the heart is closed, the left ventricle contracts, causing a volume of the fluid to be expelled from the bag, through the conduit, and into the balloon, in a manner that produces a corresponding decrease in a total volume of the ventricle during isovolumetric contraction of the ventricle. It is advantageous to reduce the volume of the ventricle during isovolumetric contraction of the ventricle in order to facilitate reverse remodeling of the ventricle, such that the heart returns to a healthy geometry. Typically, this is accomplished since this application of the invention reduces the extent to which the ventricular wall is stretched at high pressure. This yields acute and chronic reduction in ventricular wall stress, which the inventor hypothesizes will result (typically over the course of months) in the desired reverse remodeling described hereinabove.

For some applications, the bag is positionable within the left ventricle of the patient while the compliant balloon or second bag is positionable outside of the left ventricle. For example, the compliant balloon or second bag may be positionable in the right atrium, the inferior vena cava, or the superior vena cava.

For some applications of the present invention, the passive pump comprises first and second noncompliant bags. A spring is coupled to one of the bags that is designated for positioning outside of the ventricle. The spring absorbs energy during filling of the bag, e.g., typically during ventricular systole, and releases the energy in order to expel the fluid from within the bag, e.g., during ventricular diastole, and into the other bag that is disposed within the ventricle.

There is therefore provided, in accordance with an application of the present invention apparatus, including:

a flexible intraventricular receptacle configured to be positioned within a ventricle of a heart of a patient, the flexible intraventricular receptacle being configured to assume a first volume upon passage of fluid that is not blood into the flexible intraventricular receptacle and a second volume upon passage of at least part of the fluid out of the flexible intraventricular receptacle, the second volume being smaller than the first volume;

an expandable extraventricular receptacle configured to be positioned outside of the ventricle, the expandable extraventricular receptacle being configured to expand upon transfer of the fluid into the expandable extraventricular receptacle from the intraventricular receptacle and to contract upon passage of at least part of the fluid out of the expandable extraventricular receptacle; and a conduit disposed between and in fluid communication with the flexible intraventricular receptacle and the expandable extraventricular receptacle, the conduit being configured to allow passage of the fluid between the intraventricular and the extraventricular receptacles, the apparatus is configured such that when the intraventricular receptacle is disposed within the ventricle, the extraventricular receptacle is disposed outside of the ventricle, the apparatus is configured to facilitate the passage of the fluid between the intraventricular and the extraventricular receptacles responsively to a cardiac cycle of the heart, in a manner in which:

during ventricular diastole, the extraventricular receptacle contracts and expels the fluid, through the conduit, into the intraventricular receptacle, and during ventricular systole, while an aortic valve of the heart is closed, a volume of the fluid is expelled from the intraventricular receptacle, through the conduit, into the extraventricular receptacle, in a manner that produces a corresponding decrease in a total volume of the ventricle during isovolumetric contraction of the ventricle, and the apparatus further includes an energy-storage element coupled to the expandable extraventricular receptacle and configured to:

absorb energy upon filling of the expandable extraventricular receptacle from a first state to a second, expanded state, and release the energy to return the expandable extraventricular receptacle from the second, expanded state to the first state.

In an application, the extraventricular receptacle is configured to be positioned at an extracardiac location, and the conduit defines a transmyocardial conduit configured to be disposed passing through a wall of the heart.

In an application, the extraventricular receptacle includes a bellows, and the energy-storage element is coupled to the bellows in a manner in which the bellows is disposed between the intraventricular receptacle and the energy-storage element.

In an application, the energy-storage element is configured to:

assume a compressed, longitudinally-shortened state upon the filling of the bellows from the first state to the second, expanded state, and return the bellows from the second, expanded state to the first state.

In an application, the energy-storage element includes a coil spring.

In an application, the energy-storage element includes a shape-memory material.

In an application, the apparatus includes a scaffolding surrounding the bellows and the energy-storing element, and the energy-storage element is coupled at a first end of the energy-storage element to an outer surface of the bellows, and at a second end of the energy-storage element to a portion of the scaffolding, during absorbing and releasing of the energy by the energy-storage element, the first end of the energy-storage element moves, respectively, toward and away from the second end of the energy-storage element.

In an application, the extraventricular receptacle includes a bellows, and the energy-storage element is coupled to the bellows by surrounding the bellows at least in part.

In an application, the energy-storage element includes a coil spring that at least partially surrounds the bellows and is configured to:

assume a longitudinally-elongated state upon the filling of the bellows from the first state to the second, expanded state, and return the bellows from the second, expanded state to the first state.

In an application, the coil spring wraps around the bellows between folds of the bellows.

In an application, the energy-storage element includes a plurality of struts surrounding the extraventricular receptacle, a respective portion of each of the struts is configured to:

assume a longitudinally-elongated state upon the filling of the expandable extraventricular receptacle from the first state to the second, expanded state, assume a longitudinally-shortened state, and return the expandable extraventricular receptacle from the second, expanded state to the first state during a transition of the energy-storage element from the longitudinally-elongated state toward the longitudinally-shortened state.

In an application, in the longitudinally-shortened state, the respective portion of each of the struts is shaped so as to define a bend which projects laterally away from a central longitudinal axis of the apparatus.

In an application, each strut extends longitudinally along an external surface of the extraventricular receptable in a direction (1) from a portion of the extraventricular receptable that is furthest from the intraventricular receptable, and toward (2) the intraventricular receptable.

In an application, the apparatus includes a stent structure, and a first portion of the stent structure surrounds the conduit, and the energy-storage element defines a second portion of the stent structure that surround the extraventricular receptacle.

In an application:

a part of the first portion of the stent structure surrounds a portion of the intraventricular receptacle, the stent structure is (i) compressed during delivery of the apparatus into a body of a patient, and (ii) expandable during implantation of the apparatus in the body of the patient, and once expanded, the first portion of the stent structure is shaped so as to define (1) a narrowed portion at the conduit and (2) a wider portion than the narrowed portion, at the part of the first portion of the stent structure that surrounds the portion of the intraventricular receptacle.

In an application, the energy-storage element includes a mesh having a first portion surrounding the extraventricular receptacle, the first portion of the mesh is configured to:

absorb the energy upon the filling of the expandable extraventricular receptacle from the first state to the second, expanded state, and release the energy to return the expandable extraventricular receptacle from the second, expanded state to the first state.

In an application, the apparatus is configured such that as the first portion of the mesh releases the energy, the first portion of the mesh transitions toward a longitudinally-shortened state in which the first portion of the mesh expands radially and shortens longitudinally, with respect to a central longitudinal axis of the apparatus.

In an application, a second portion of the mesh surrounds the conduit, and a third portion of the mesh surrounds a portion of the intraventricular receptacle.

In an application:
the mesh is (i) compressed during delivery of the apparatus into a body of a patient, and (ii) expandable during implantation of the apparatus in the body of the patient, and
once expanded, the second portion of the mesh is shaped so as to define a narrowed portion at the conduit and the third portion of the mesh is shaped so as to define a wider portion than the narrowed portion, at the portion of the intraventricular receptacle.

In an application, the apparatus further includes the fluid, and the fluid has a volume of 10-80 ml which is passable between the flexible intraventricular receptacle and the expandable extraventricular receptacle via the conduit.

In an application, the intraventricular receptacle is an intra-left-ventricular receptacle.

In an application, the apparatus further includes a stent structure, and the stent structure surrounds the conduit.

In an application, the apparatus further includes a scaffolding disposed within the intraventricular receptacle, the scaffolding being configured to prevent dislodging of the intraventricular receptacle from within the ventricle.

In an application, the apparatus further includes a rod disposed within the intraventricular receptacle, the rod being configured to prevent dislodging of the intraventricular receptacle from within the ventricle.

In an application, the expandable extraventricular receptacle is compliant.

In an application, wall compliance of the expandable extraventricular receptacle is at least three times wall compliance of the flexible intraventricular receptacle.

In an application, the expandable extraventricular receptacle and the flexible intraventricular receptacle are configured such that, in the absence of any external forces applied to the expandable extraventricular receptacle and the flexible intraventricular receptacle, (a) the expandable extraventricular receptacle undergoes an increase in volume when exposed to a change in internal pressure from 10 mmHg to 120 mmHg that is at least three times greater than (b) an increase in volume that the flexible intraventricular receptacle undergoes when exposed to a change in internal pressure from 10 mmHg to 120 mmHg.

In an application, the expandable extraventricular receptacle and the flexible intraventricular receptacle are configured such that, in the absence of any external forces applied to the expandable extraventricular receptacle and the flexible intraventricular receptacle, (a) the expandable extraventricular receptacle undergoes an increase in volume when exposed to a change in internal pressure from 10 mmHg to 120 mmHg that is at least 200%, and (b) the flexible intraventricular receptacle undergoes an increase in volume when exposed to a change in internal pressure from 10 mmHg to 120 mmHg that is less than 120%.

There is also provided, in accordance with an application of the present invention a method for repairing a heart, including:

identifying a heart of a patient as having a reduced ejection fraction; and
in response to the identifying, reducing wall stress of a ventricle of the heart by implanting apparatus that facilitates cyclical moving of fluid that is not blood of the patient into and out of the ventricle of the heart, the moving including:
during ventricular diastole, moving a volume of the fluid into the ventricle in a manner that produces a corresponding decrease in a total volume of blood that fills the ventricle during diastole; and
during ventricular systole, moving the volume of the fluid out of the ventricle in a manner that produces a corresponding decrease in a total volume of the ventricle during isovolumetric contraction of the ventricle.

In an application, implanting the apparatus includes reducing a volume of blood expelled by the ventricle during systole.

In an application, moving the volume of the fluid out of the ventricle includes moving the volume of the fluid out of the heart.

In an application, implanting the apparatus includes implanting apparatus including a bag, a compliant balloon and a conduit disposed between and in fluid communication with the bag and the compliant balloon, in a manner in which (1) the bag is disposed within the ventricle, and (2) the compliant balloon is disposed outside the ventricle.

In an application, wall compliance of the balloon is at least three times wall compliance of the bag.

In an application, the bag is noncompliant.

In an application, implanting the apparatus includes positioning the bag in a left ventricle.

In an application, implanting the apparatus includes positioning the bag in a right ventricle.

In an application, implanting the apparatus includes:
positioning the balloon at an extracardiac space, and
positioning the conduit transmyocardially.

In an application, implanting the apparatus includes positioning the balloon in a right atrium, and the method further includes implanting the apparatus in a manner in which the conduit extends from the left ventricle to the right atrium.

In an application, implanting the apparatus includes positioning the balloon in a superior vena cava, and the method further includes implanting the apparatus in a manner in which the conduit extends from the left ventricle to the superior vena cava.

In an application, implanting the apparatus includes positioning the balloon in an inferior vena cava, and the method further includes implanting the apparatus in a manner in which the conduit extends from the left ventricle to the inferior vena cava.

In an application, implanting apparatus includes implanting apparatus including a first bag, a second bag and a conduit disposed between and in fluid communication with the first bag and the second bag, in a manner in which (1) the first bag is disposed within the ventricle, and (2) the second bag is disposed outside the ventricle.

In an application, the first and second bags are noncompliant.

In an application, implanting the apparatus includes positioning the first bag in a left ventricle.

In an application, implanting the apparatus includes positioning the first bag in a right ventricle.

In an application, implanting the apparatus includes:
positioning the second bag at an extracardiac space, and
positioning the conduit transmyocardially.

In an application, implanting the apparatus includes positioning the second bag in a right atrium, and the method further includes implanting the apparatus in a manner in which the conduit extends from the left ventricle to the right atrium.

In an application, implanting the apparatus includes positioning the second bag in a superior vena cava, and the method further includes implanting the apparatus in a manner in which the conduit extends from the left ventricle to the superior vena cava.

In an application, implanting the apparatus includes positioning the second bag in an inferior vena cava, and the method further includes implanting the apparatus in a manner in which the conduit extends from the left ventricle to the inferior vena cava.

In an application, the apparatus includes an energy-storage element coupled to the second bag and configured to:
  absorb energy upon filling of the second bag from a first state to a second, expanded state, and
  release the energy to return the second bag from the second, expanded state to the first state.

In an application, the energy-storage element includes a plurality of struts surrounding the second bag, a respective portion of each of the struts is configured to:
  assume a longitudinally-elongated state upon the filling of the second bag from the first state to the second, expanded state,
  assume a longitudinally-shortened state, and
  return the second bag from the second, expanded state to the first state during a transition of the energy-storage element from the longitudinally-elongated state toward the longitudinally-shortened state.

In an application, the energy-storage element includes a mesh having a first portion surrounding the second bag, the first portion of the mesh is configured to:
  absorb the energy upon the filling of the second bag from the first state to the second, expanded state, and
  release the energy to return the second bag from the second, expanded state to the first state.

In an application, the second bag includes a bellows, and the energy-storage element is coupled to the bellows.

In an application, implanting the apparatus includes acutely further reducing the ejection fraction and chronically increasing the ejection fraction.

There is further provided, in accordance with an application of the present invention apparatus, including:
  an intraventricular bag configured to be positioned within a ventricle of a heart of a patient, the bag having, in the absence of any external forces applied thereto: (a) a first intraventricular bag volume when the bag has an internal pressure of 120 mmHg, and (b) a second intraventricular bag volume when the bag has an internal pressure of 10 mmHg, the first intraventricular bag volume being less than 110% of the second intraventricular bag volume;
  an extraventricular bag configured to be positioned outside of the ventricle, the extraventricular bag having, in the absence of any external forces applied thereto: (a) a first extraventricular bag volume when the extraventricular bag has an internal pressure of 120 mmHg, and (b) a second extraventricular bag volume when the extraventricular bag has an internal pressure of 10 mmHg, the first extraventricular bag volume being at least 200% of the second extraventricular bag volume;
  a conduit disposed between and in fluid communication with the intraventricular bag and the extraventricular bag, the apparatus thereby defining a total internal space disposed within the conduit, the intraventricular bag, and the extraventricular bag; and
  disposed within the internal space, 10-80 ml of fluid that is (a) not blood and (2) passable between the intraventricular bag and the extraventricular bag via the conduit,
  the apparatus is configured such that:
    during ventricular diastole, the extraventricular bag expels the fluid, through the conduit, and into the intraventricular bag, and
    during ventricular systole, while an aortic valve of the heart is closed, a volume of the fluid is expelled from the intraventricular bag, through the conduit, into the extraventricular bag, and
  the apparatus further includes an energy-storage element coupled to the extraventricular bag and configured to:
    absorb energy upon filling of the extraventricular bag from a first state to a second, expanded state, and
    release the energy to return the extraventricular bag from the second, expanded state to the first state.

In an application, the extraventricular receptacle is configured to be positioned at an extracardiac location, and the conduit defines a transmyocardial conduit configured to be disposed passing through a wall of the heart.

In an application, the energy-storage element includes a plurality of struts surrounding the extraventricular bag, a respective portion of each of the struts is configured to:
  assume a longitudinally-elongated state upon the filling of the extraventricular bag from the first state to the second, expanded state,
  assume a longitudinally-shortened state, and
  return the extraventricular bag from the second, expanded state to the first state during a transition of the energy-storage element from the longitudinally-elongated state toward the longitudinally-shortened state.

In an application, the energy-storage element includes a mesh having a first portion surrounding the extraventricular bag, the first portion of the mesh is configured to:
  absorb the energy upon the filling of the extraventricular bag from the first state to the second, expanded state, and
  release the energy to return the extraventricular bag from the second, expanded state to the first state.

In an application, the extraventricular bag includes a bellows, and the energy-storage element is coupled to the bellows in a manner in which the bellows is disposed between the first bag and the energy-storage element.

In an application, the energy-storage element is configured to:
  assume a compressed, longitudinally-shortened state upon the filling of the bellows from the first state to the second, expanded state, and
  return the bellows from the second, expanded state to the first state.

In an application, the energy-storage element includes a coil spring.

In an application, the extraventricular bag includes a bellows, and the energy-storage element is coupled to the bellows by surrounding the bellows at least in part.

In an application, the energy-storage element includes a coil spring that at least partially surrounds the bellows and is configured to:
  assume a longitudinally-elongated state upon the filling of the bellows from the first state to the second, expanded state, and
  return the bellows from the second, expanded state to the first state.

In an application, the coil spring wraps around the bellows between folds of the bellows.

There is also provided, in accordance with an application of the present invention apparatus, including:

a first bag having, in the absence of any external forces applied thereto: (a) a first first-bag volume when the first bag has an internal pressure of 120 mmHg, and (b) a second first-bag volume when the first bag has an internal pressure of 10 mmHg, the first first-bag volume being less than 110% of the second first-bag volume;

a second bag having, in the absence of any external forces applied thereto: (a) a first second-bag volume when the second bag has an internal pressure of 120 mmHg, and (b) a second second-bag volume when the second bag has an internal pressure of 10 mmHg, the first second-bag volume being less than 110% of the second second-bag volume;

an energy-storage element coupled to the second bag and configured to:

absorb energy upon filling of the second bag from the first second-bag volume to the second second-bag volume, and release the energy to return the second bag from the second second-bag volume to the first second-bag volume;

a conduit disposed between and in fluid communication with the first bag and the second bag, the apparatus thereby defining a total internal space disposed within the conduit, the first bag, and the second bag; and disposed within the internal space, 10-80 ml of fluid that is (a) not blood and (b) passable between the first bag and the second bag via the conduit.

In an application, the second bag is configured to be positioned at an extracardiac location, and the conduit defines a transmyocardial conduit configured to be disposed passing through a wall of the heart.

In an application, the energy-storage element includes a plurality of struts surrounding the second bag, a respective portion of each of the struts is configured to:

assume a longitudinally-elongated state upon the filling of the second bag from the first state to the second, expanded state, assume a longitudinally-shortened state, and return the second bag from the second, expanded state to the first state during a transition of the energy-storage element from the longitudinally-elongated state toward the longitudinally-shortened state.

In an application, the energy-storage element includes a mesh having a first portion surrounding the second bag, the first portion of the mesh is configured to:

absorb the energy upon the filling of the second bag from the first state to the second, expanded state, and release the energy to return the second bag from the second, expanded state to the first state.

In an application, the second bag includes a bellows, and the energy-storage element is coupled to the bellows in a manner in which the bellows is disposed between the first bag and the energy-storage element.

In an application, the energy-storage element is configured to:

assume a compressed, longitudinally-shortened state upon the filling of the bellows from the first state to the second, expanded state, and return the bellows from the second, expanded state to the first state.

In an application, the energy-storage element includes a coil spring.

In an application, the second bag includes a bellows, and the energy-storage element is coupled to the bellows by surrounding the bellows at least in part.

In an application, the energy-storage element includes a coil spring that at least partially surrounds the bellows and is configured to:

assume a longitudinally-elongated state upon the filling of the bellows from the first state to the second, expanded state, and return the bellows from the second, expanded state to the first state.

In an application, the coil spring wraps around the bellows between folds of the bellows.

The present invention will be more fully understood from the following detailed description of applications thereof, taken together with the drawings, in which:

BRIEF DESCRIPTION OF THE DRAWINGS

FIG. 2 is a schematic illustration of implantation of the passive pump, in accordance with some applications of the present invention;

FIGS. 7A-B, 8, and 9 are schematic illustrations of the operation of a passive pump, in accordance with respective applications of the present invention;

FIGS. 12A-B are schematic illustrations of a passive pump comprising two noncompliant bags and a spring comprising a plurality of struts, in accordance with some applications of the present invention;

FIGS. 15A-B are schematic illustrations of a passive pump comprising two noncompliant bags and bellows surrounded by a spring, in accordance with some applications of the present invention.

DETAILED DESCRIPTION OF EMBODIMENTS

Figures 1A, 1B:
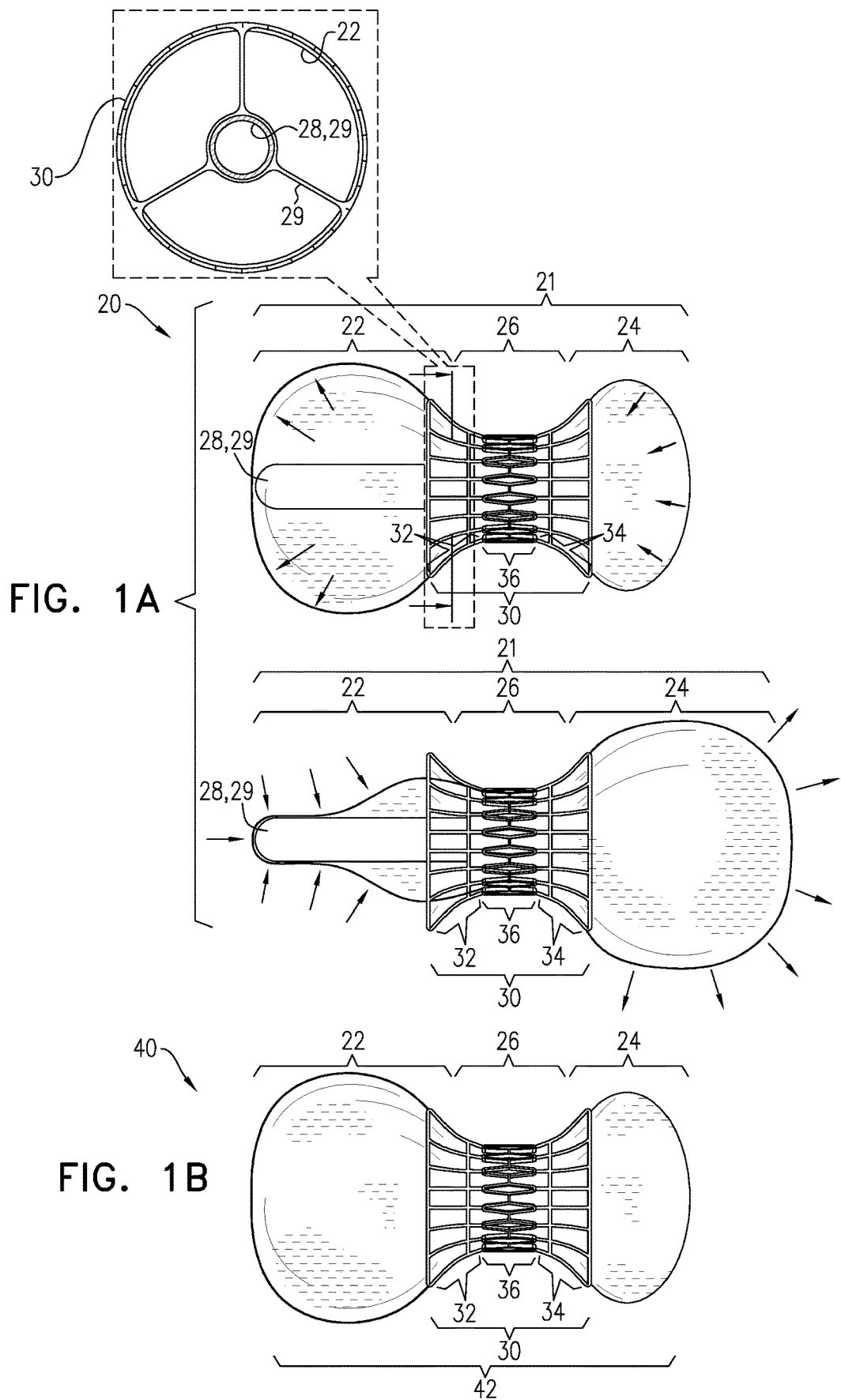
FIGS. 1A-B are schematic illustrations of a passive pump comprising a noncompliant bag and a compliant balloon, in accordance with respective applications of the present invention.

Reference is now made to FIG. 1A, which is a schematic illustration of a system 20 comprising a passive pump 21 which comprises a noncompliant bag 22 and a compliant balloon 24, in accordance with some applications of the present invention. A conduit 26 is disposed between and in fluid communication with bag 22 and compliant balloon 24. Passive pump 21 defines a total internal space disposed within conduit 26, bag 22, and compliant balloon 24. Fluid is disposed within the internal space and is passable between bag 22 and compliant balloon 24 via conduit 26. Typically, the internal space contains 10-80 ml of fluid, e.g., 20-40 ml of fluid. Typically, the fluid comprises fluid that is not blood of the patient. For some applications of the present invention, the fluid comprises a gas, such as carbon dioxide, or a liquid, such as saline. Alternatively or additionally, the fluid comprises a reduced-osmolarity fluid, e.g., a contrast-agent fluid which is used for imaging and is known to be acceptable for use in contact with blood of a patient. (It is expected that in general, there will be no contact between the fluid and the patient's blood.)

Bag 22 comprises a noncompliant, biocompatible material, e.g., polyethylene terephthalate (PET). Balloon 24 comprises a compliant, biocompatible material, e.g., polyolefin copolymer (POC), silicone, or polyurethane. For some applications of the present invention, wall compliance of the balloon 24 is at least three times wall compliance of bag 22.

Passive pump 21 is configured for implantation at a heart of a patient. Typically, bag 22 is designated for positioning within a ventricle of the patient. For some applications, bag 22 is designated for positioning within a left ventricle of the heart of the patient. Alternatively, bag 22 is designated for positioning within a right ventricle of the heart of the patient. Thus, bag 22 defines a flexible, intraventricular receptacle. Balloon 24 is designated for positioning outside of the ventricle. For some applications, balloon 24 is designated for positioning outside of the heart of the patient. In such applications, balloon 24 defines an expandable extracardiac receptacle, and conduit 26 defines a transmyocardial conduit disposed between and in fluid communication with the flexible intraventricular receptacle (e.g., bag 22) and the expandable extracardiac receptacle (e.g., balloon 24). For applications in which conduit 26 is positioned transmyocardially, as shown in FIGS. 2, 3A-G, and 5, conduit 26 typically has an inner diameter of 6-10 mm, and a length of 2-5 cm, e.g., 3 cm.

For some applications, balloon 24 is designated for positioning outside of the ventricle of the heart of the patient (e.g., in the right atrium as shown in FIGS. 7A-B, for example, in the superior vena cava, as shown in FIG. 8, for example, or in the inferior vena cava, as shown in FIG. 9, for example). In such applications, balloon 24 defines an expandable extraventricular receptacle, and conduit 26 defines a conduit disposed between and in fluid communication with the flexible intraventricular receptacle (e.g., bag 22) and the expandable extraventricular receptacle (e.g., balloon 24).

For some applications, balloon 24 is configured to be positioned at a site within the patient's vascular system, e.g., in a right atrium of the heart of the patient, or in the patient's superior vena cava or inferior vena cava, as shown in FIGS. 7A-B, 8 and 9.

That is, for generally all applications of the present invention, balloon 24 of FIGS. 1A-3G and 5 defines an extraventricular receptacle.

Reference is now made to FIGS. 1A-B, 2, 3A-G, 4A-B, 5, 6A-B, 7A-B, 8-11, 12A-B, 13A-B, 14A-B, and 15A-B. Passive pumps 21, 42, 82, 92, 182, 202, 302, 402, and 502 are configured for facilitating reverse remodeling in the heart of a patient experiencing heart failure. Passive pumps 21, 42, 82, 92, 182, 202, 302, 402, and 502 are configured, during ventricular systole, while an aortic valve of the heart is closed, for enabling passage of fluid that is not blood of the patient from within the ventricle to outside of the ventricle in a manner that produces a corresponding decrease in a total volume of the ventricle during isovolumetric contraction of the ventricle. That is, for example, since passive pump 21 is passive and bag 22 is noncompliant, some volume of the fluid exits the ventricle by exiting bag 22 during ventricular diastolic filling, such that pressure in the heart begins to rise at a lower total volume of the ventricle at the onset of isovolumetric contraction of the ventricle. Ultimately, passive pumps 21, 42, 82, 92, 182, 202, 302, 402, and 502 enable reverse remodeling of the heart because the left ventricle does not undergo as high wall stress while containing a high volume of blood, at the onset of and/or during isovolumetric contraction of the ventricle, as would occur in the absence of the applications of the present invention described herein.

Passive pumps 21, 42, 82, 92, 182, 202, 302, 402, and 502 are passive in that their respective systems 20, 40, 60, 90, 100, 120, 180, 200, 300, 400, and 500 do not require any electrical or other source of power for the passive pumps to move the fluid within the pump. Additionally, passive pumps 21, 42, 82, 92, 182, 202, 302, 402, and 502 do not facilitate acute therapeutic motion of the ventricular wall, and do not acutely therapeutically push the ventricular wall, myocardium and/or the epicardium with a force originated due to energy harvested by the system from a motion of the ventricular chamber. Rather, passive pumps 21, 42, 82, 92, 182, 202, 302, 402, and 502 function responsively to a cardiac cycle of the heart in a manner in which, for example:

at the onset of and during ventricular diastole, due to decreased pressure in the left ventricle, the extraventricular receptacle (e.g., balloon 24) contracts (as shown in the upper figure in FIG. 1A, for example) and begins to expel the fluid, through the conduit (e.g., the transmyocardial conduit, for example conduit 26), into the intraventricular receptacle (e.g., bag 22), and during ventricular systole, and even slightly before, while the aortic valve of the heart is closed, a volume of the fluid is expelled from the intraventricular receptacle (e.g., bag 22), through the conduit (e.g., the transmyocardial conduit, for example conduit 26), into the extraventricular receptacle (e.g., balloon 24), in a manner that produces a corresponding decrease in a total volume of the ventricle during isovolumetric contraction of the ventricle.

Thus, due to the cyclical moving of fluid that is not blood into and out of the ventricle, passive pumps 21, 42, 82, 92, 182, 202, 302, 402, and 502 cause acute as well as chronic reduction in wall stress of cardiac muscle surrounding the ventricle at the onset of ventricular systole. Additionally, for some embodiments of the present invention, passive pumps 21, 42, 82, 92, 182, 202, 302, 402, and 502 also cause the ejection fraction of the heart and the cardiac output to be (1) even further acutely reduced in patients that have been identified as already having a reduced ejection fraction and cardiac output, and (2) chronically increased. At the onset of and during ventricular diastole, systems 20, 40, 60, 90, 100, 120, 180, 200, 300, 400, and 500 enable the moving of a volume of the fluid within passive pumps 21, 42, 82, 92, 182, 202, 302, 402, and 502 into the ventricle in a manner that produces a corresponding decrease in a total volume of blood that fills the ventricle during diastole. During ventricular systole and even slightly before, systems 20, 40, 60, 90, 100, 120, 180, 200, 300, 400, and 500 enable moving the volume of the fluid within the pump out of the ventricle in a manner that produces a corresponding decrease in a total volume of the ventricle during isovolumetric contraction of the ventricle.

FIG. 1A shows passive pump 21 in a state in which fluid is distributed in a manner in which fluid is passed into bag 22 such that bag 22 assumes a larger volume (upper image) than when the fluid is passed out of bag 22 and into balloon 24 (lower image) so that bag 22 assumes a lower volume. As fluid passes out of bag 22 and into balloon 24, balloon 24 fills and/or expands to assume a larger volume (lower image) than when less fluid is disposed within balloon 24 (upper image). Since balloon 24 is compliant, it contracts to expel fluid disposed therein. Typically, one or more of the following numerical characteristics applies to bag 22 and balloon 24:

- In the absence of external force applied to balloon 24 (e.g., the expandable extraventricular receptacle) and bag 22 (e.g., the flexible intraventricular receptacle), balloon 24 typically undergoes an increase in volume when exposed to a change in internal pressure from 10 mmHg to 120 mmHg that is at least three (e.g., at least five) times greater than any increase in volume that bag 22 undergoes when exposed to a change in internal pressure from 10 mmHg to 120 mmHg
- In the absence of any external forces applied to balloon 24 (e.g., expandable extraventricular receptacle) and to bag 22 (e.g., the flexible intraventricular receptacle), (a) balloon 24 undergoes an increase in volume when exposed to a change in internal pressure from 10 mmHg to 120 mmHg that is at least 200%, and (b) (i) the volume of bag 22 having 120 mmHg internal pressure is less than (ii) a volume that is greater than 20% more than the volume of bag 22 having 10 mmHg internal pressure (and is for some applications substantially the same as the volume of bag 22 having 10 mmHg internal pressure).
- In the absence of any external forces applied to bag 22, (a) a first bag volume of bag 22 is 10-80 ml (e.g., 40 ml) when the intraventricular receptacle has an internal pressure of 120 mmHg, and (b) a second bag volume of bag 22 is 10-80 ml (e.g., 40 ml) when the bag has an internal pressure of 10 mmHg. Additionally, the first bag volume is less than 110% of the second bag volume. The second bag volume is typically within 10% of the first bag volume, e.g., the first and second bag volumes are substantially the same, because bag 22 is non-compliant.
- In the absence of any external forces applied to balloon 24, balloon 24 has (a) a first balloon volume of at least 30 ml, e.g., 80 ml, when balloon 24 has an internal pressure of 120 mmHg, and (b) a second balloon volume of at least 10 ml, e.g., 20 ml, when balloon 24 has an internal pressure of 10 mmHg.

It is to be noted that the passage of a given volume of fluid out of bag 22 corresponds to a similar or identical passage of fluid into balloon 24 and vice versa. That is, a volume increase in one receptacle substantially corresponds to a volume decrease in another receptacle.

Since bag 22 is configured for positioning within the ventricle, bag 22 is subjected to high pressure from the ventricle. As such, a fixation rod 28 is typically disposed within bag 22 which reinforces bag 22 and prevents everting and/or migration of bag 22 out of the ventricle. For some applications of the present invention, rod 28 is part of a scaffolding 29 disposed within bag 22. For some applications of the present invention, rod 28 prevents everting of bag 22 through the transmyocardial access point of passive pump 21 to the ventricle. For some applications in which balloon 24 is positioned outside of the heart, balloon 24 may be surrounded by an optional cage (not shown). The cage may help protect balloon 24 by encasing balloon 24 or it may help facilitate expansion of balloon 24 by providing a defined space in which balloon 24 is allowed to expand.

Conduit 26 is reinforced, e.g., by being surrounded or internally lined, by a stent structure 30. Structure 30 comprises a central tubular substructure 36, a first flared section 32 which is configured to surround a portion of bag 22, and a second flared section 34 which is configured to surround a portion of balloon 24.

For applications in which conduit 26 is configured to be positioned within tissue of the patient, e.g., within myocardial tissue, conduit 26 comprises a tube surrounded by porous material, e.g., a fabric, which facilitates tissue growth around conduit 26 in order to enable sealing of conduit 26 and inhibit leakage of blood out of the ventricle. For some applications of the present invention, conduit 26 self-expands to position itself within the tissue of the patient.

Reference is now made to FIG. 1B, which is a schematic illustration of a system 40 comprising a passive pump 42 which comprises a noncompliant bag 22 and a compliant balloon 24, in accordance with some applications of the present invention. A conduit 26 is disposed between and in fluid communication with bag 22 and compliant balloon 24. Passive pump 42 defines a total internal space disposed within conduit 26, bag 22, and compliant balloon 24. Fluid is disposed within the internal space and is passable between bag 22 and compliant balloon 24 via conduit 26. It is to be noted that system 40 is similar to and used in a similar fashion as system 20 described hereinabove with reference to FIG. 1A, like reference numbers referring to like parts, with the exception that passive pump 42 does not comprise rod 28 and scaffolding 29.

FIG. 2 is a schematic illustration of implantation passive pump 21 of FIG. 1A, in accordance with some applications of the present invention. Typically, passive pump 21 is delivered transapically for applications in which passive pump 21 is configured to be positioned transmyocardially such that bag 22 is positioned within a ventricle 50 while balloon 24 is positioned at an extracardiac location. For some applications, passive pump 21 is delivered using a sub-xyphoid approach. Passive pump 21 is delivered to the heart in a compressed state within a delivery tool 58. A distal portion of delivery tool 58 is passed through myocardial tissue 53 at apex 51 of the heart. Delivery tool 58 enables bag 22 to be positioned within a space of ventricle 50. Tool 58 pushes passive pump 21 distally and/or tool 58 is retracted proximally in order to expose flared section 32 of stent structure 30 such that flared section 32 expands against and engages a wall of ventricle 50. For some applications, flared section 32 comprises a biocompatible material is coated with a porous material, e.g., a fabric, which helps facilitate sealing of flared section 32 with respect to cardiac tissue by enhancing tissue growth into the outer surface of flared section 32. Flared section 32 facilitates fixation of bag 22 in ventricle 50. Flared section 32 is shaped so as to allow for bag 22 to fill and take shape as shown in the upper figure of FIG. 1A. Tool 58 is then further retracted so that central tubular substructure 36 expands within and engages myocardial tissue 53. Central tubular substructure 36 comprises a biocompatible material surrounded by porous material, e.g., a fabric, which helps facilitate sealing of central tubular substructure 36 with respect to cardiac tissue by enhancing tissue growth into substructure 36. Tool 58 is then yet further retracted, so that flared section 34 expands against and engages the epicardium of the heart. For some applications, flared section 34 comprises a biocompatible material coated by a porous material, e.g., a fabric, which helps facilitate sealing of flared section 34 with respect to cardiac tissue by enhancing tissue growth into flared section 34. Flared section 34 facilitates fixation of balloon 24 at the extracardiac location. Flared section 34 is shaped so as to allow for balloon 24 to fill, expand, and take shape as shown in the lower figure of FIG. 1A.

Reference is now made to FIGS. 3A-G, which are schematic illustrations of the operation of passive pump 21 of FIG. 1A, in accordance with some applications of the present invention. Passive pump 42 operates in a like manner.

Figure 3A:
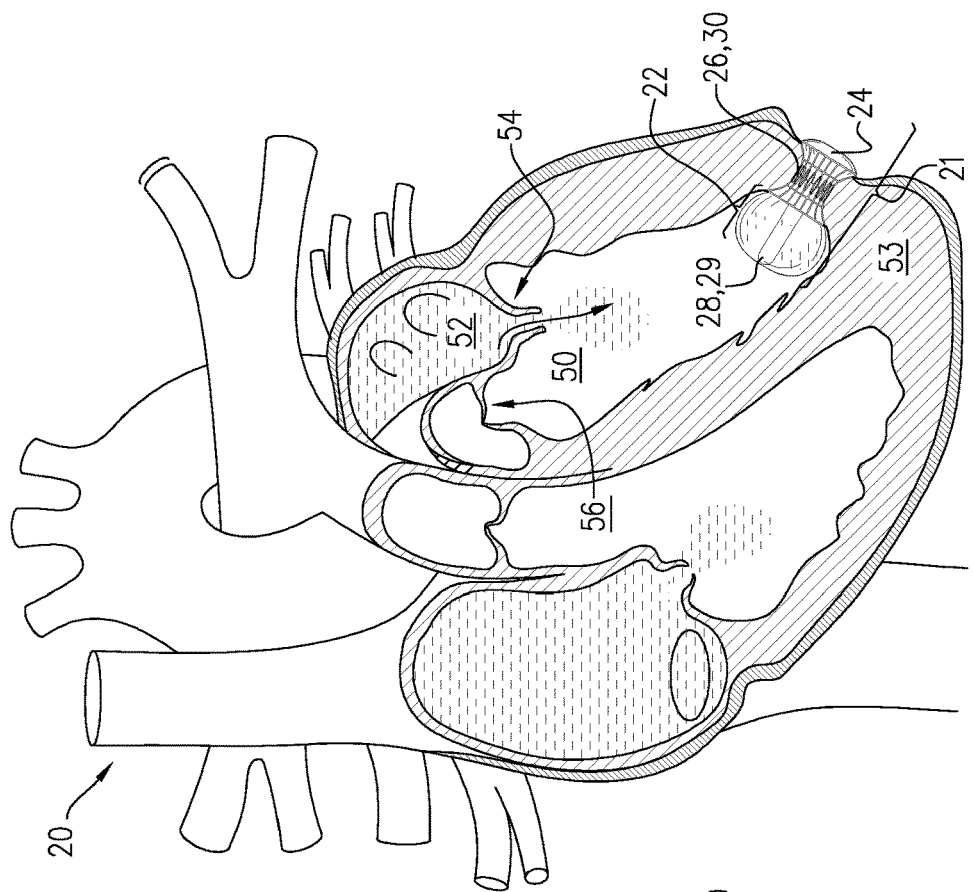
FIGS. 3A-G are schematic illustrations of the operation of the passive pump, in accordance with some applications of the present invention.
Figure 3B:
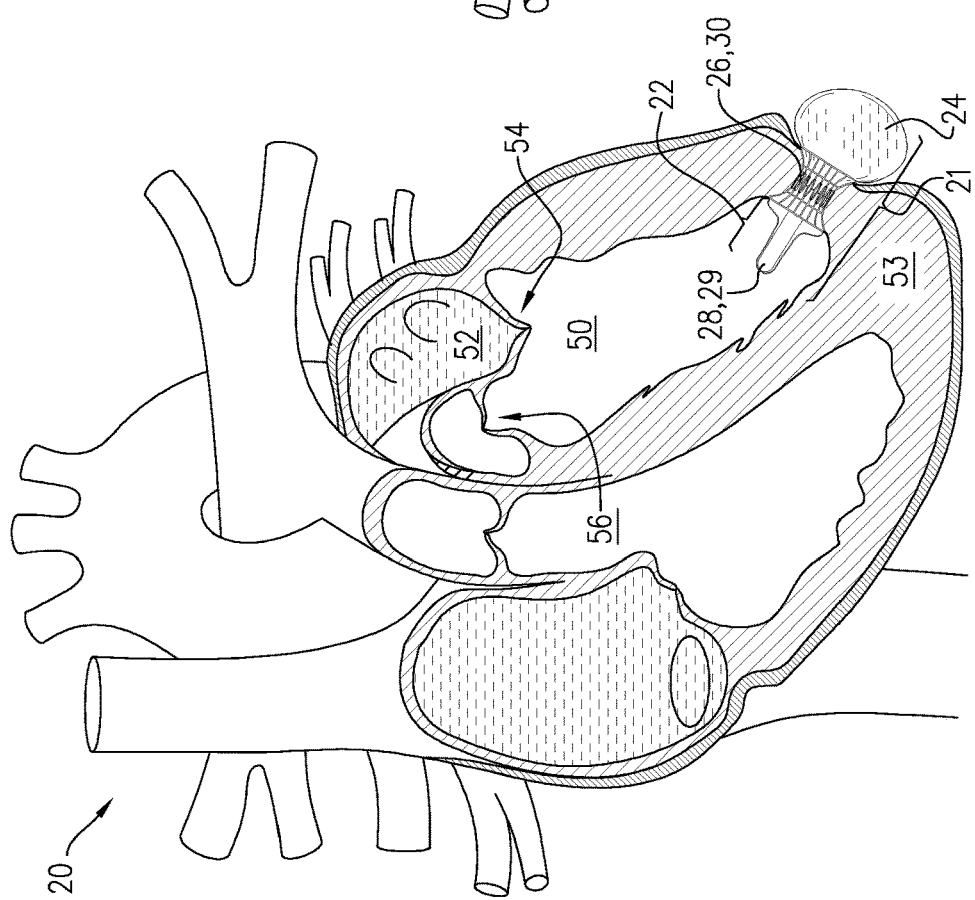
Figure 3C:
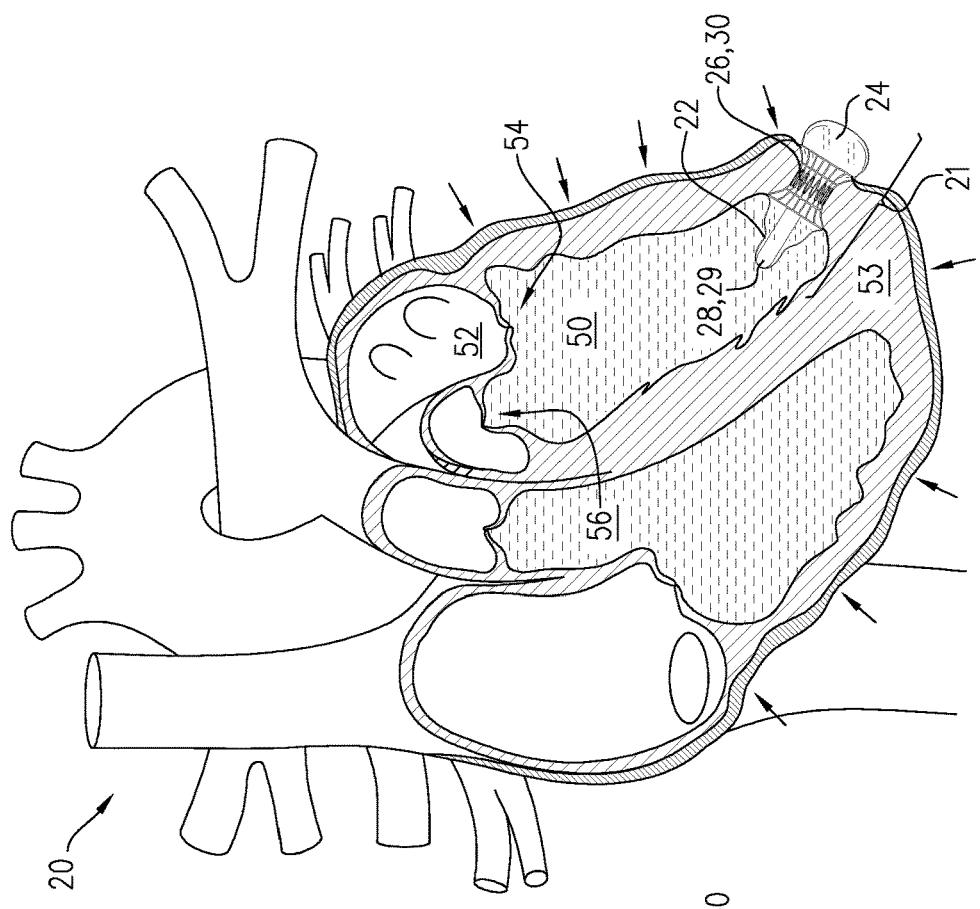
Figure 3D:
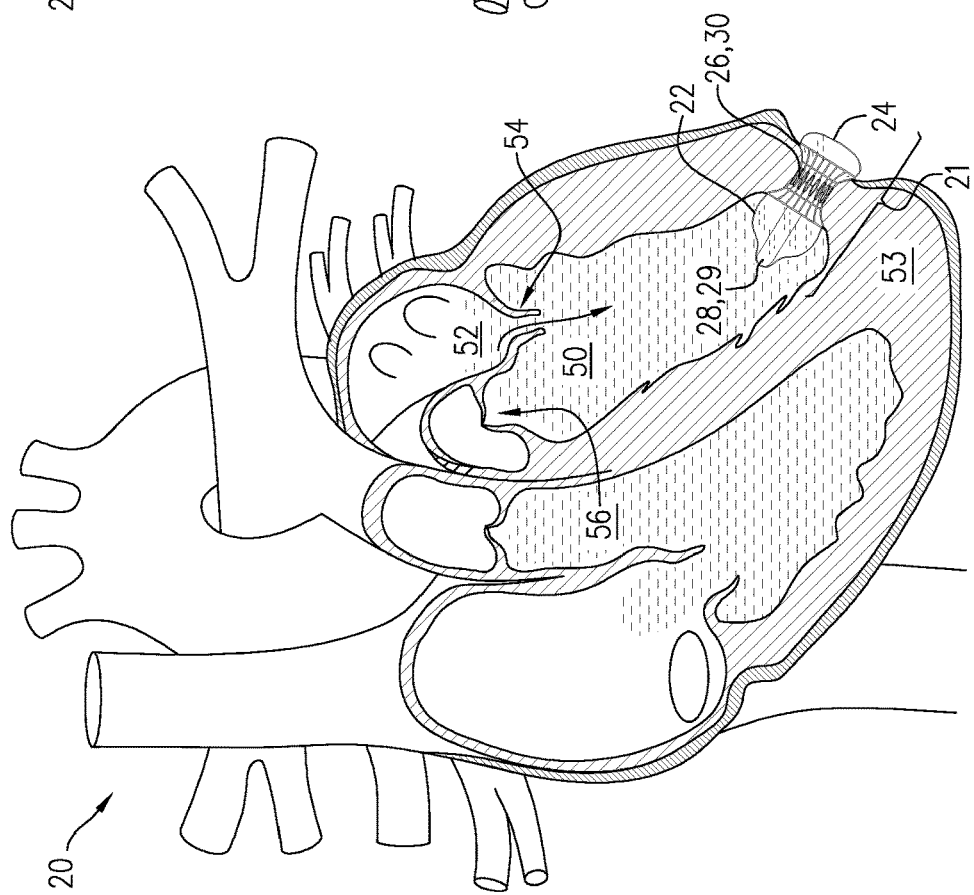
Figure 3F:
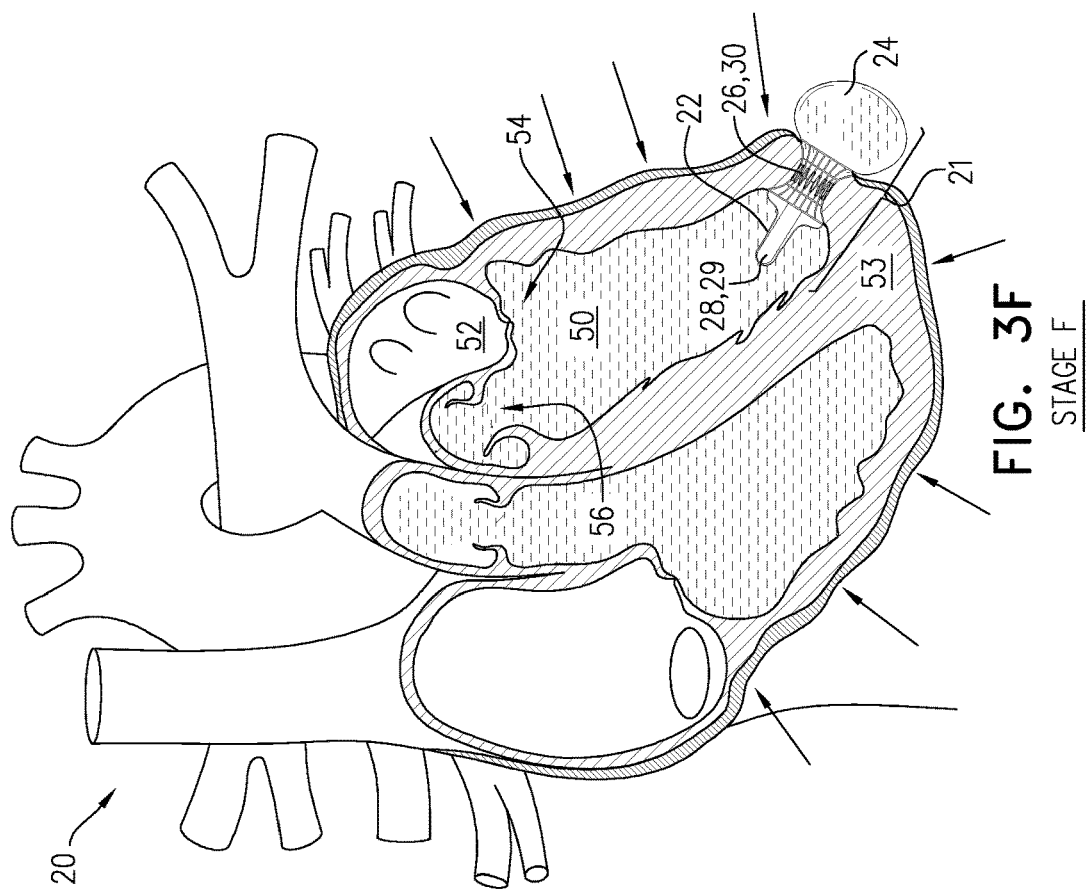
Figure 3E:
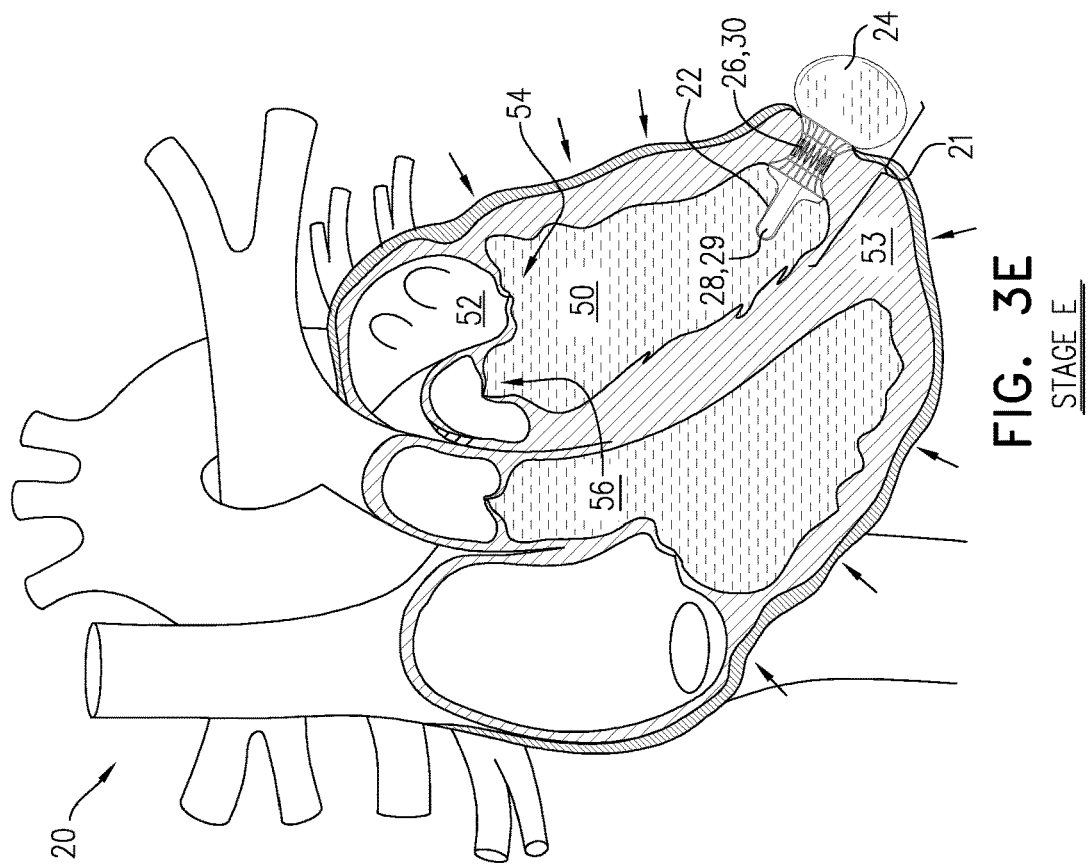
Figure 3G:
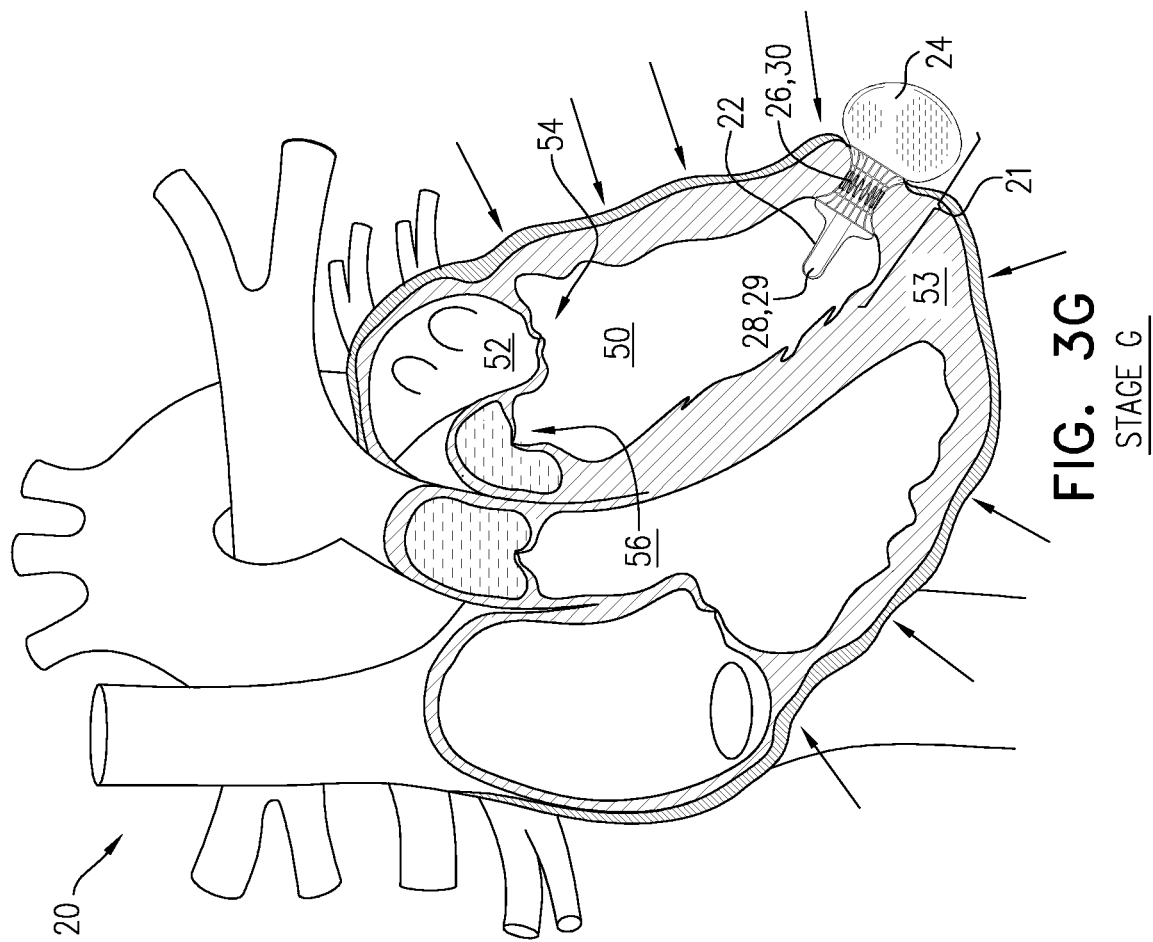
Figures 4A, 4B:
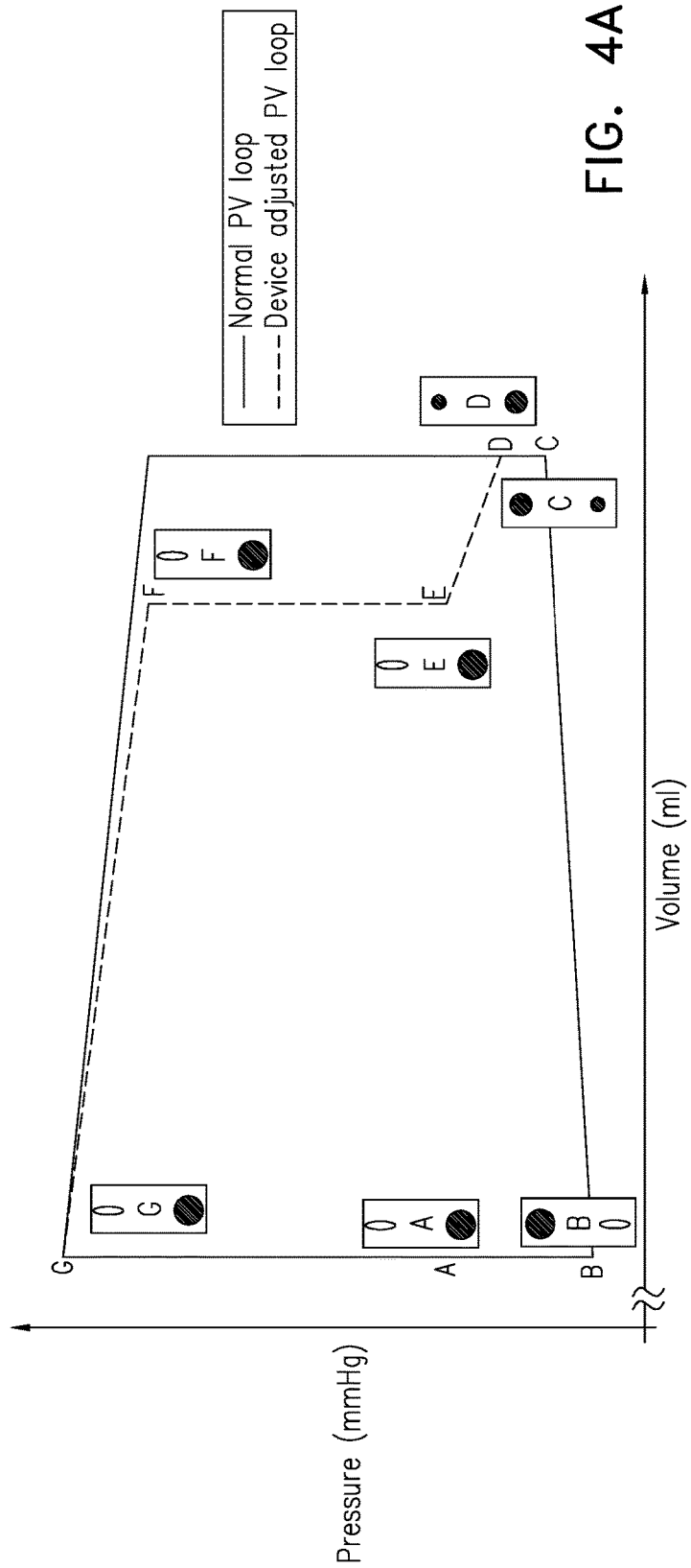
FIG. 4A is a graph and FIG. 4B is a table representing the association between the cardiac cycle and operation of the passive pump as shown in FIGS. 3A-G, in accordance with some applications of the present invention.

Reference is now made to FIG. 4A, which is a graph and to FIG. 4B, which is a table representing the association between the cardiac cycle and operation of passive pump 21 as shown in FIGS. 3A-G, as well as passive pumps 42, 82, 92, 182, 202, 302, 402, and 502, mutatis mutandis, in accordance with some applications of the present invention.

FIG. 3A shows a Stage A in which the heart undergoes isovolumetric relaxation while mitral valve 54 is closed and aortic valve 56 is closed. Stage A is when the heart undergoes diastole and blood has not yet entered left ventricle 50. The volume in ventricle 50 is low and the pressure decreases. At Stage A, pressure in ventricle 50 is still sufficiently high (as shown in the near-bottom left side of the graph in FIG. 4A) that fluid from within passive pump 21 does not yet enter bag 22 disposed within ventricle 50 and remains within balloon 24 in its expanded state. Balloon 24 assumes a volume in its expanded state of for example 20-80 ml, e.g., 40 ml. As shown in FIG. 3A, bag 22 assumes a very low volume and is near to empty or empty of the fluid. Rod 28 and scaffolding 29 maintain bag 22 from escaping from ventricle 50 by everting through myocardial tissue 53.

Once the pressure in ventricle 50 drops to Stage B as represented in FIG. 3B and in the bottom left corner of the graph on FIG. 4A, balloon 24 contracts due to its compliance and due to the reduced pressure in ventricle 50, and expels the fluid through transmyocardial conduit 26 and into bag 22 within left ventricle 50. Bag 22 fills to assume a greater volume than the volume it assumes in Stage A. Bag 22 fills to a volume of 20-80 ml, e.g., 40 ml. As shown in FIG. 3B, balloon 24 has a very low volume and is near to empty or empty of the fluid.

Since (1) passive pump 21 is constructed in a manner in which bag 22 comprises a noncompliant material and balloon 24 is compliant, and (2) fluid passes between balloon 24 into bag 22 responsively to changes in pressure within ventricle 50, passive pump 21 operates passively and in response to the cardiac cycle.

At Stage B, the heart is in diastole, and mitral valve 54 begins to open and blood begins to enter left ventricle 50 from left atrium 52. Aortic valve 56 remains closed. Bag 22, in its filled state, occupies space within ventricle 50 while blood of the patient fills ventricle 50. Moving the volume of the fluid into ventricle 50, i.e., into bag 22, produces a corresponding decrease in a total volume of blood that fills ventricle 50 during diastole as is shown in FIG. 3C.

FIG. 3C shows Stage C, in which the diastolic phase is near completion and mitral valve 54 begins to close. Aortic valve 56 remains closed. Ventricle 50 is close to full with blood. Due to the volume of blood in ventricle 50, some of the fluid within bag 22 is pushed into balloon 24. At Stage C, the pressure in ventricle 50 is increased more than the pressure at Stage B.

Reference is now made to FIG. 3D, which shows the heart in a stage of isovolumetric contraction at the onset of systole. Both aortic valve 56 and mitral valve 54 are closed. Once mitral valve 54 is closed, the pressure due to the volume of blood in ventricle 50 and ventricular contraction pushes the fluid from bag 22 into balloon 24, such that bag 22 decreases in volume and balloon 24 increases in volume. Thus, pressure in ventricle 50 forces the fluid from within bag 22 through conduit 26 and into balloon 24. Movement of the volume of fluid out of the heart and into balloon 24 produces a corresponding decrease in a total volume of ventricle 50 during isovolumetric contraction of ventricle 50. It is advantageous to reduce the volume of ventricle 50 during isovolumetric contraction of ventricle 50 in order to facilitate reverse remodeling of the ventricle such that the heart returns to a healthy geometry. Reducing the volume of ventricle 50 increase the ventricular wall thickness during contraction, thereby reducing wall stress in the ventricle wall. The reduced stress on the ventricle wall enables the wall to gradually return to its normal non-stretched geometry, i.e., to undergo reverse remodeling.

That is, with reference to the graph of FIG. 4A, the pressure of the ventricle isovolumetrically increases at a lower volume (as depicted by the dotted line representing the device-adjusted PV loop) rather than at a higher volume (as depicted by the solid line representing the normal PV loop). Lower volume during contraction yields less exertion per cubic millimeter of ventricular wall tissue, enabling the heart to heal and reverse-remodel. Thus, without the assistance of the passive pumps described herein, the pathologically remodeled heart would otherwise follow the graph represented by the solid line; that is, ventricle 50 would begin increasing in pressure during the isovolumetric phase of systole at a greater volume of ventricle 50, thereby increasing stress in tissue of the ventricle wall. However, with the assistance of the passive pumps 21, 42, 82, 92, 182, 202, 302, 402, and 502, the remodeled, stretched ventricle 50 instead follows the graph represented by the dotted line; that is, ventricle 50 begins increasing in pressure during the isovolumetric phase of systole at a lower volume of ventricle 50, thereby reducing the stress on tissue of the ventricle wall. Thus, the assistance of passive pumps 21, 42, 82, 92, 182, 202, 302, 402, and 502 generates acute as well as chronic reduction in wall stress of cardiac muscle surrounding the ventricle at the onset of ventricular systole due to cyclical moving of fluid that is not blood of the patient into and out of ventricle 50, i.e., into and out of bag 22 and balloon 24 of passive pumps 21, 42, 82, 92, 182, 202, 302, 402, and 502. Additionally, for some embodiments of the present invention, passive pumps 21, 42, 82, 92, 182, 202, 302, 402, and 502 also generate (1) an acute further reducing of the ejection fraction of the heart due to cyclical moving of fluid that is not blood of the patient into and out of ventricle 50, i.e., into and out of the intraventricular receptacle and the extraventricular receptacle of passive pumps 21, 42, 82, 92, 182, 202, 302, 402, and 502 as well as (2) a chronic increase in ejection fraction. This acute further reduction of the ejection fraction reduces the stress on the ventricle.

In FIG. 3E, left ventricle 50 increases in pressure and continues isovolumetric contraction while mitral valve 54 and aortic valve 56 remain closed in Stage E. The increase in pressure in ventricle 50 together with the ventricle having filled with blood pushes the remaining fluid out of bag 22 and through conduit 26 and into balloon 24 in a manner in which bag 22 is near to empty or empty. Balloon 24 fills to hold the volume of fluid that was occupying space in ventricle 50 (FIGS. 3B-D) just before the onset of isovolumetric contraction. Moving the volume of fluid out of ventricle 50 produces a corresponding decrease in volume of ventricle 50 during isovolumetric contraction.

In Stage F as shown in FIG. 3F, aortic valve 56 opens and the ejection stage of systole commences while the pressure in ventricle 50 increases due to the contraction of ventricle 50 in order to eject the blood. A lower volume of blood passes through aortic valve 56 during ejection than would otherwise pass through valve 56 in the absence of passive pump 21.

At the end of systole, as shown in Stage G of FIG. 3G, the blood has been ejected from ventricle 50, however, the pressure in ventricle 50 is still high such that the fluid remains in balloon 24. Aortic valve 56 is closed and the heart initiates isovolumetric relaxation. Once ventricle 50 sufficiently reduces in pressure during the isovolumetric relaxation stage of diastole, the heart returns to Stage A shown in FIG. 3A. Once the pressure in ventricle is low enough (Stage B of FIGS. 3B and 4A), balloon 24 contracts due to its compliance and expels the fluid back into bag 22 (FIG. 3B), and the cycle repeats.

Figure 5:
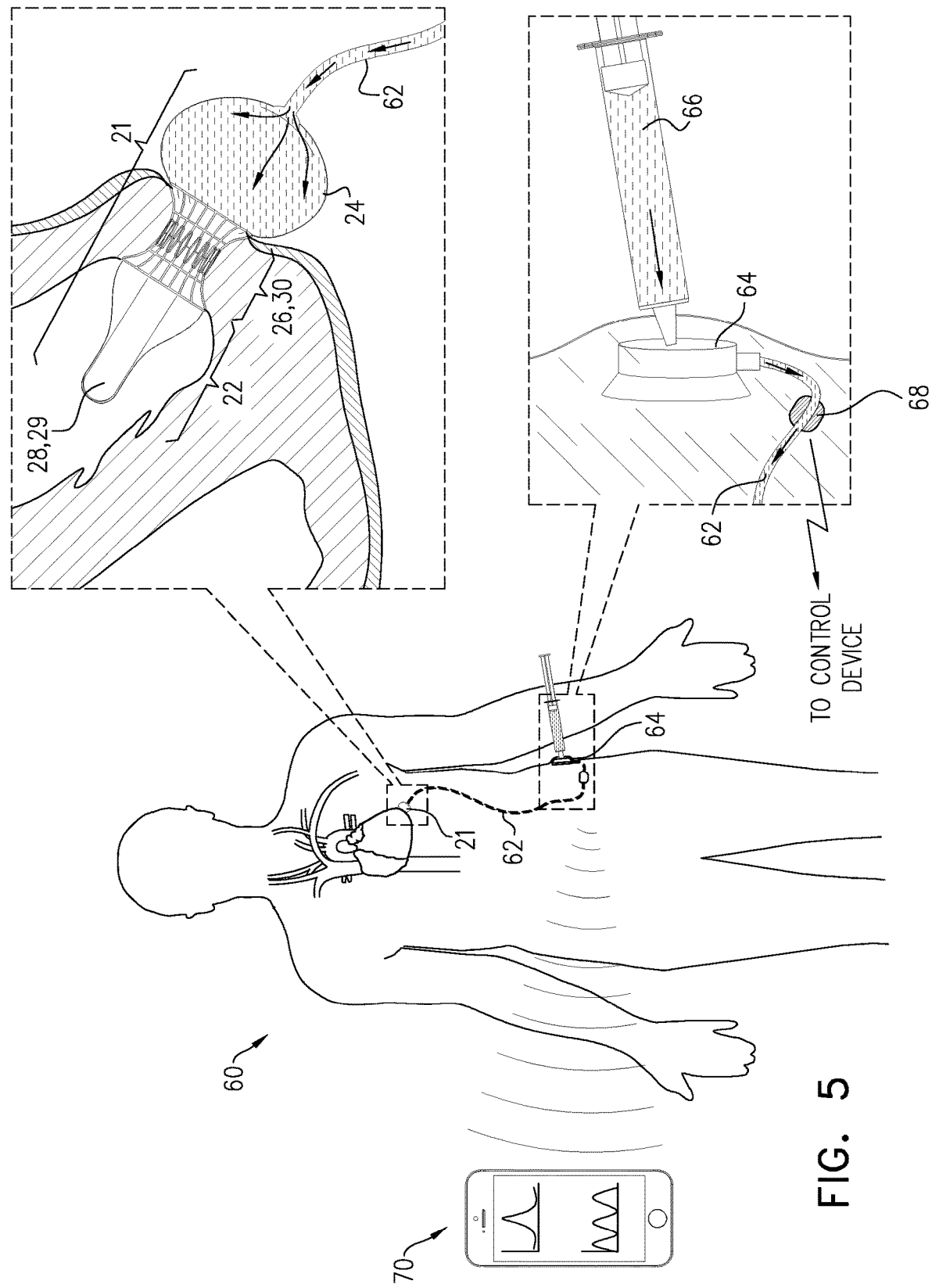
FIG. 5 is a schematic illustration of a port system connected to the passive pump, in accordance with some applications of the present invention.

Reference is now made to FIG. 5, which is a schematic illustration of a system 60 comprising a port 64 connected to passive pump 21 of FIG. 1A, in accordance with some applications of the present invention. Port 64 comprises a typically subcutaneous port which enables the physician to control a volume of fluid in passive pump 21. For some applications of the present invention, passive pump 21 is implanted without any fluid, and the operating physician injects fluid into passive pump 21 via port 64. For other applications, passive pump 21 is implanted with fluid and system 60 enables the physician to inject and/or extract fluid depending on the need of the patient. Port 64 comprises a membrane that is penetrable by a needle connected to a syringe 66 filled with fluid designated for injection through port 64, through a tube 62 connecting port 64 to passive pump 21 and into the internal space defined by passive pump 21. For some applications (as shown), tube 62 is coupled to balloon 24 by way of illustration and not limitation. For example, tube 62 may alternatively be connected to conduit 26 or to bag 22.

Port 64 may be placed subcutaneously at the waist of the patient as shown, or at any suitable location in the body of the patient, e.g., the chest.

For some applications, a pressure sensor 68 (e.g., coupled to tube 62) senses the pressure in passive pump 21 and wirelessly transmits to an external device 70 information relating to the pressure in passive pump 21. Sensor 68 may be coupled to tube 62 at any suitable location along tube 62 or to any portion of passive pump 21. For some applications of the present invention, a coil is coupled to sensor 68 for supplying power to sensor 68. For some applications of the present invention, sensor 68 is powered by radiofrequency or ultrasound energy. For some applications, the pressure measurement happens when the patient is in the doctor's office and the power antenna (e.g., radiofrequency transmitter or ultrasound transmitter) is placed next to the patient's chest. Based on the reading from sensor 68, the physician decides whether to add fluid to pump 21 or to remove fluid from pump 21.

For some applications of the present invention, two pressure sensors are coupled to conduit 26, e.g., at either end of conduit 26 in order to measure flow through conduit 26. The two pressure sensors allow the physician to derive the volume of each of bag 22 and balloon 24. That is, in response to calculation of the difference in pressure between the two sensors, the physician can determine in which of either receptacle the pressure is higher. For example, if it is sensed and determined that the pressure in bag 22 is higher than the pressure in balloon 24, then it can be determined that the flow is going from bag 22 to balloon 24.

Reference is now made to FIGS. 1A-5. It is to be noted that for some applications, instead of comprising balloon 24 at the extraventricular location, passive pumps 21 and 42 may comprise a second noncompliant bag having the same or similar properties as bag 22.

Figure 6A:
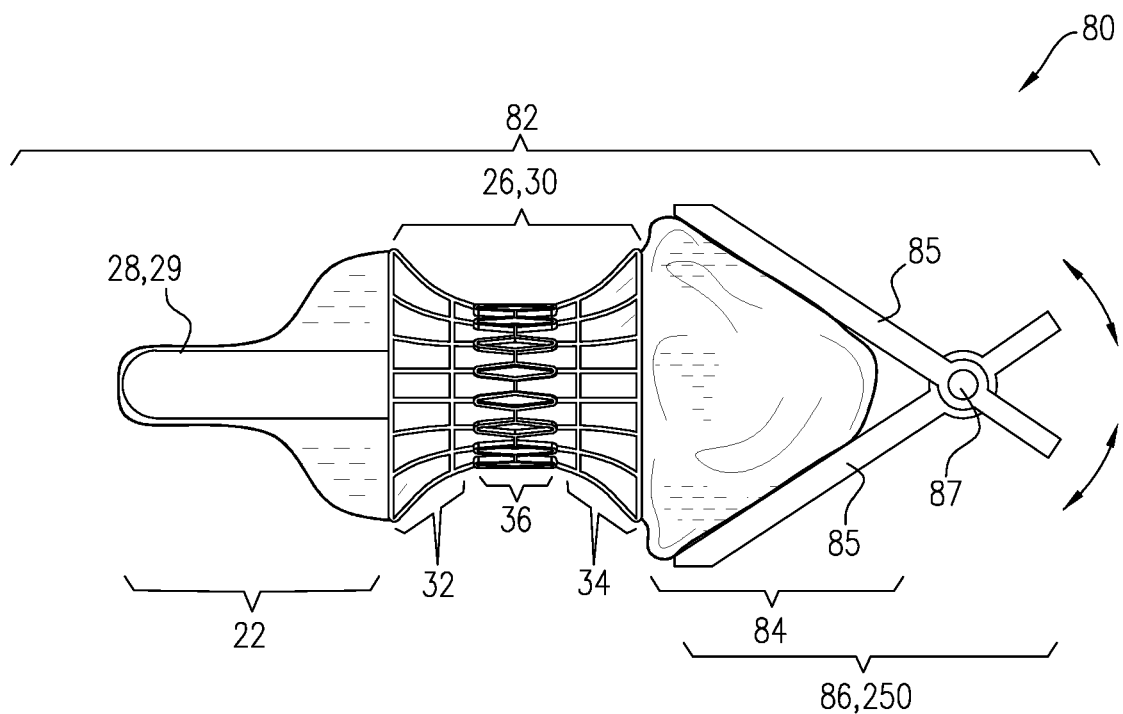
FIGS. 6A-B are schematic illustrations of a passive pump comprising two noncompliant bags and a spring, in accordance with some applications of the present invention.
Figure 6B:
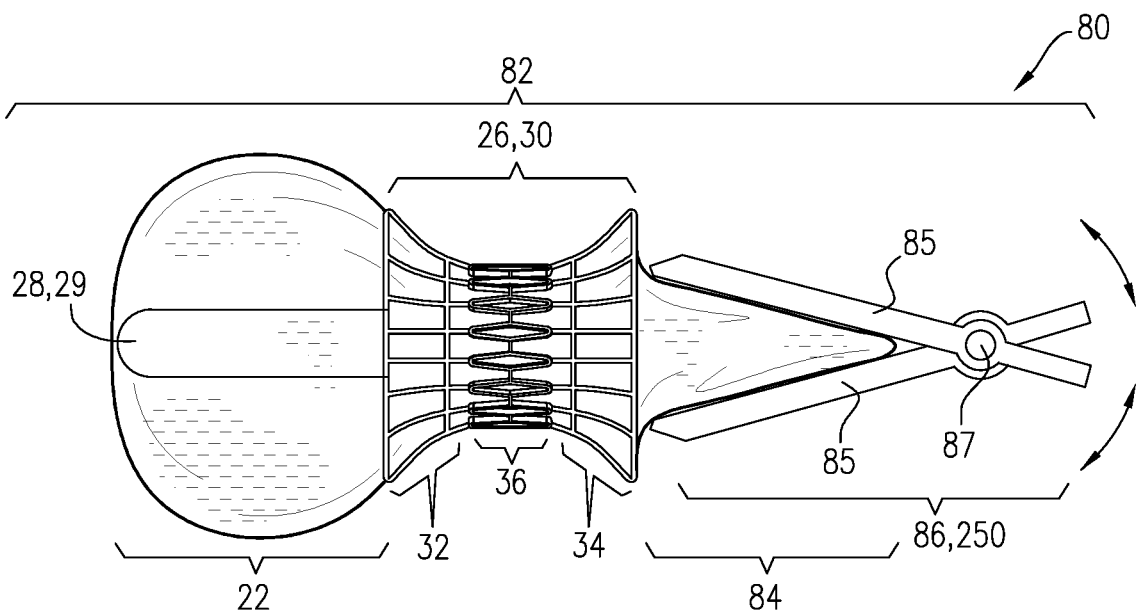

FIGS. 6A-B are schematic illustrations of a system 80 comprising a passive pump 82 comprising two bags 22 and 84 and an energy-storage element 250 comprising a spring 86, in accordance with some applications of the present invention. It is to be noted that system 80 is similar to system 20 described hereinabove with reference to FIG. 1A, like reference numbers referring to like parts, with the exception that passive pump 82 does not comprise compliant balloon 24. Bags 22 and 84 have similar wall compliance (for example, effectively no compliance at pressures less than 120 mmHg). For some applications, each of bags 22 and 84 has, in the absence of any external forces applied thereto: (a) a first volume when bags 22 and 84 each has an internal pressure of 120 mmHg, and (b) a second volume when the bags 22 and 84 each has an internal pressure of 10 mmHg, the first volume being less than 110% of the second volume.

Fluid is disposed within the internal space and is passable between bags 22 and 84 via conduit 26. Typically, the internal space contains 10-80 ml of fluid, e.g., 20-40 ml of fluid. Typically, the fluid comprises fluid that is not blood of the patient. For some applications of the present invention, the fluid comprises a gas, such as carbon dioxide, or a liquid, such as saline.

It is to be noted that bag 84 has little to no wall compliance, however, the presence of energy-storage element 250 (e.g., spring 86) imparts compliance to the section of passive pump 82 that comprises bag 84 and energy-storage element 250 (e.g., spring 86).

Spring 86 comprises two broad structural elements 85 that are coupled together by a spring hinge 87. Spring 86 is coupled to an external surface of bag 84. Spring 86 has an energy-storage state (FIG. 6A) upon bag 84 assuming a greater volume, and an energy-released state (FIG. 6B).

Once the pressure in the ventricle decreases during diastole, spring 86 releases the energy stored in it, expelling the fluid from within bag 84 into bag 22. That is, spring 86 is configured to (1) absorb energy upon filling of bag 84 (i.e., the extraventricular receptacle) from a first state to a second, expanded state (FIG. 6A), and (2) release the energy to return bag 84 (i.e., the extraventricular receptacle) from the second, expanded state to the first state (FIG. 6B).

It is to be noted that spring 86 comprises structural elements 85 and hinge 87 by way of illustration and not limitation and that spring 86 may comprise a spring having any suitable shape (e.g., helical).

Reference is now made to FIGS. 3A-G, 4A-B, and 6A-B. It is to be noted that passive pump 82 as described with reference to FIGS. 6A-B operates in Stages A-G as described in accordance with the operation of passive pump 21 with reference to FIGS. 3A-G, the graph of FIG. 4A, and the table of FIG. 4B, mutatis mutandis. For such applications, bag 84 is an extraventricular receptacle.

Reference is now made to FIGS. 1A-3G, 5, and 6A-9. It is to be noted that systems 20, 40, 60, 90, 100, and 120 may comprise energy-storage elements 250 described herein, and balloon 24 may comprise a bag such as a noncompliant bag. For example, e.g., the extraventricular receptacle may be coupled to (1) spring 86, as described hereinabove with reference to FIGS. 6A-B, (2) stent structure 250a comprising a plurality of struts 206 as described hereinbelow with reference to FIGS. 12A-B, or (3) mesh 250b as described hereinbelow with reference to FIGS. 13A-B. For other applications, the extraventricular receptacle may comprise a bellows 406 or 506 coupled to coil springs 250c and 250d, respectively, as described hereinbelow with reference to FIGS. 14A-15B.

Reference is now made to FIGS. 7A-B, which are schematic illustrations of a system 90 comprising a passive pump 92 in which a receptacle comprising a bag 96 is positioned within left ventricle 50 and a second receptacle 94 is positioned in a right atrium 55, in accordance with some applications of the present invention. Typically, a conduit 98 connects bag 96 and receptacle 94. Conduit 98 passes through mitral valve 54 and crosses the interatrial septum, e.g., via the fossa ovalis and into right atrium 55. Conduit 98 typically comprises a tube having an inner diameter of at least 5 mm in order to allow for passing of fluid between bag 96 and receptacle 94. For some applications of the present invention, passive pump 92 comprises stent structure 30 surrounding the portion of conduit 98 designated for passing through the interatrial septum or through the fossa ovalis (not shown). For some applications, conduit 98 may comprise a tube covered in a porous material, e.g., a fabric, which enhances ingrowth of tissue into the outer surface of conduit 98 in order to seal conduit 98 within the interatrial septal tissue and prevent leaking.

For some applications, bag 96 is similar to or the same as bag 22 described hereinabove with reference to FIGS. 1A-B, 2, 3A-G, 4A-B, 5, and 6A-B. That is, bag 96 is noncompliant.

For some applications, receptacle 94 is similar to or the same as balloon 24 described hereinabove with reference to FIGS. 1A-B, 2, 3A-G, 4A-B, and 5. That is, receptacle 94 is compliant and has wall compliance. Receptacle 94 is considered an extraventricular receptacle.

For some applications, receptacle 94 is similar to bag 22 described hereinabove with reference to FIGS. 1A-B, 2, 3A-G, 4A-B, 5, and 6A-B or to bag 84 described hereinabove with reference to FIGS. 6A-B (even without utilizing spring 86). That is, receptacle 94 is noncompliant. In such applications fluid passes from receptacle 94 to bag 96 disposed within left ventricle 50 when pressure in left ventricle 50 reduces from around 120 mmHg to around 5 mmHg. Since pressure in right atrium 55 remains around 15 mmHg, when pressure in left ventricle 50 drops to around 5 mmHg in Stage B (described hereinabove with reference to FIG. 3B), for example, as shown in FIG. 7A, fluid passes from receptacle 94 within right atrium 55 and into bag 96 disposed within left ventricle 50.

In FIG. 7B, left ventricle 50 increases in pressure and continues isovolumetric contraction while mitral valve 54 and aortic valve 56 remain closed in Stage E (as described hereinabove with reference to FIG. 3E). The increase in pressure in ventricle 50 together with the ventricle having filled with blood pushes the fluid out of bag 96 and through conduit 98 and into receptacle 94 in a manner in which bag 96 is near to empty or empty. Receptacle 94 fills to hold the volume of fluid that was occupying space in ventricle 50 (FIGS. 3B-D) just before the onset of isovolumetric contraction. Moving the volume of fluid out of ventricle 50 produces a corresponding decrease in volume of ventricle 50 during isovolumetric contraction.

Reference is now made to FIGS. 3A-G, 4A-B, 7A-B, and 8-9. It is to be noted that passive pump 92 as described with reference to FIGS. 7A-B and 8-9 operates in Stages A-G as described in accordance with the operation of passive pump 21 with reference to FIGS. 3A-G, the graph of FIG. 4A, and the table of FIG. 4B, mutatis mutandis.

Reference is now made to FIGS. 6A-B, 7A-B, 8-9, and 12A-15B. It is to be noted that systems 90, 100, and 120 may comprise energy-storage elements 250 described herein (e.g., spring 86 coupled to receptacle 94 as described hereinabove with reference to FIGS. 6A-B, stent structure 250a comprising a plurality of struts 206 as described hereinbelow with reference to FIGS. 12A-B, mesh 250b as described hereinbelow with reference to FIGS. 13A-B, and coil springs 250c and 250d as described hereinbelow with reference to FIGS. 14A-15B). Additionally, fluid is disposed within the internal space and is passable between receptacle 94 and bag 96 via conduit 98. Typically, the internal space contains 10-80 ml of fluid, e.g., 20-40 ml of fluid. Typically, the fluid comprises fluid that is not blood of the patient. For some applications of the present invention, the fluid comprises a gas, such as carbon dioxide, or a liquid, such as saline.

Reference is again made to FIGS. 7A-B. Passive pump 92 is implanted using a transcatheter/transvascular approach and advantageously does not require making an incision in myocardial tissue of the heart of the patient.

For some applications, conduit 98 travels from bag 96, through a hole made in the interventricular septum, through the tricuspid valve, and to receptacle 94 positioned in right atrium 55.

Reference is now made to FIG. 8, which is a schematic illustration of a system 100 comprising passive pump 92 in which bag 96 is positioned within left ventricle 50 and receptacle 94 is positioned in the superior vena cava 102, in accordance with some applications of the present invention. Receptacle 94 is an extraventricular receptacle. It is to be noted that system 100 is similar to system 90 described hereinabove with reference to FIGS. 7A-B, like reference numbers referring to like parts, with the exception that passive receptacle 94 of pump 92 is positioned in superior vena cava 102.

Reference is now made to FIG. 9, which is a schematic illustration of a system 120 comprising passive pump 92 in which bag 96 is positioned within left ventricle 50 and receptacle 94 is positioned in the inferior vena cava 122, in accordance with some applications of the present invention. It is to be noted that system 120 is similar to system 90 described hereinabove with reference to FIGS. 7A-B, like reference numbers referring to like parts, with the exception that passive receptacle 94 of pump 92 is positioned in inferior vena cava 122. Receptacle 94 is an extraventricular receptacle.

Reference is now made to FIGS. 7A-B and 8-9. It is to be noted that bag 96 may be positioned within the right ventricle. It is to be additionally noted that, for some applications, use of gas within pump 92 may be preferable for embodiments in which pump 92 is positioned intravascularly.

Figure 10:
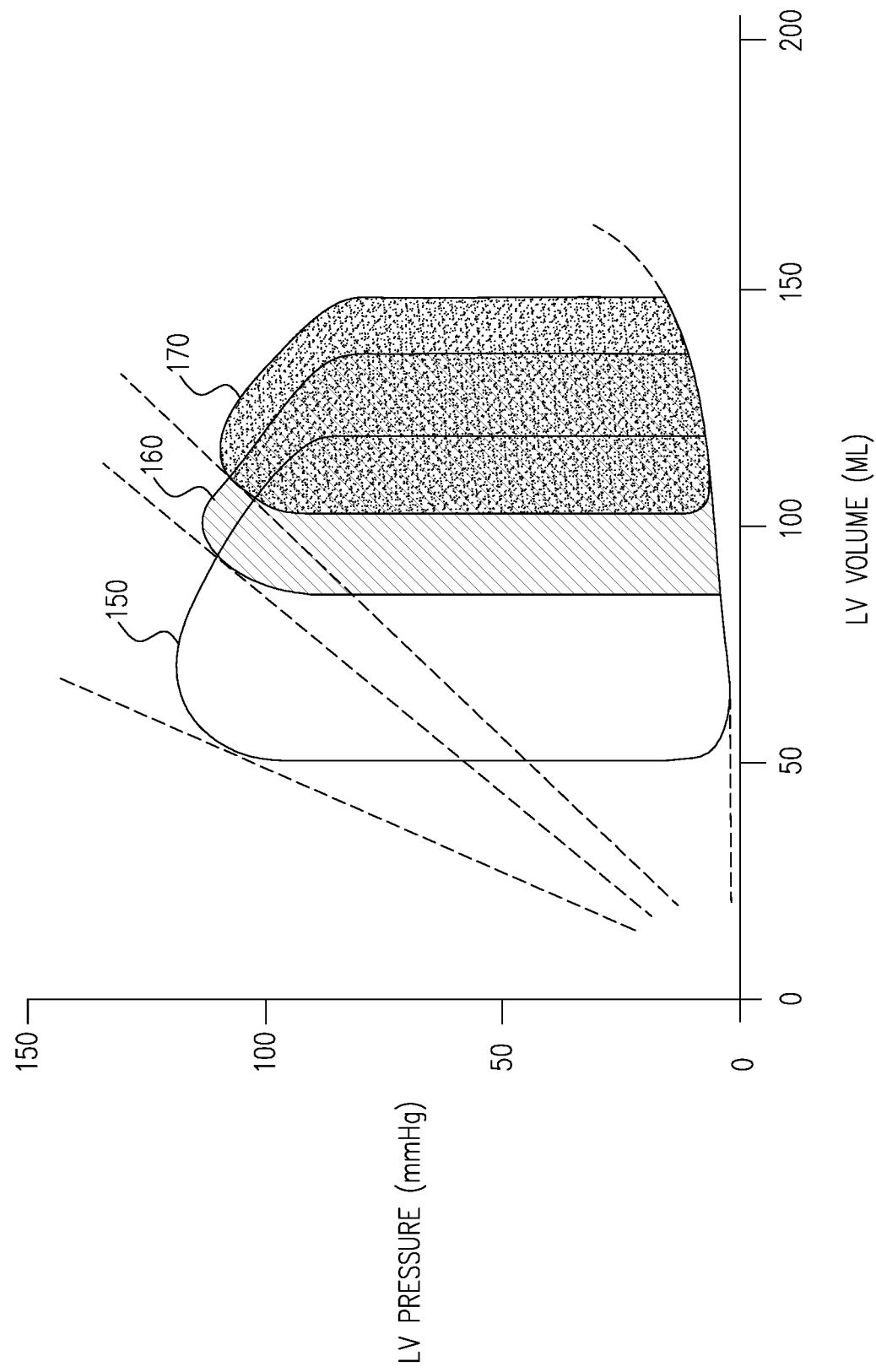
FIG. 10 is a pressure/volume graph illustrating the respective pressure/volume loops of a failing heart, a healthy heart, and a heart with the passive pump, in accordance with some applications of the present invention.

Reference is now made to FIG. 10, which is a pressure/volume graph illustrating a pressure/volume loop 170 of a failing heart, a pressure/volume loop 150 of a healthy heart, and a pressure/volume loop 160 of a heart with the passive pumps described herein, in accordance with some applications of the present invention. Pressure/volume loop 170 of a failing heart shows reduced stroke volume increased left ventricular end-diastolic pressure and volume.

Reference is now made to FIGS. 1A-B, 2, 3A-G, 4A-B, 5, 6A-B, 7A-B, 8-11, 12A-B, 13A-B, 14A-B, and 15A-B. Upon implantation of passive pumps 21, 42, 82, 92, 182, 202, 302, 402, and 502 described herein, the pressure/volume curve shifts left (i.e., loop 160), resulting in an increase in stroke volume and a decrease in end-diastolic pressure and end-diastolic volume as compared to loop 170. This shift in the loop toward loop 160 enables the heart to reverse remodel.

Figure 11:
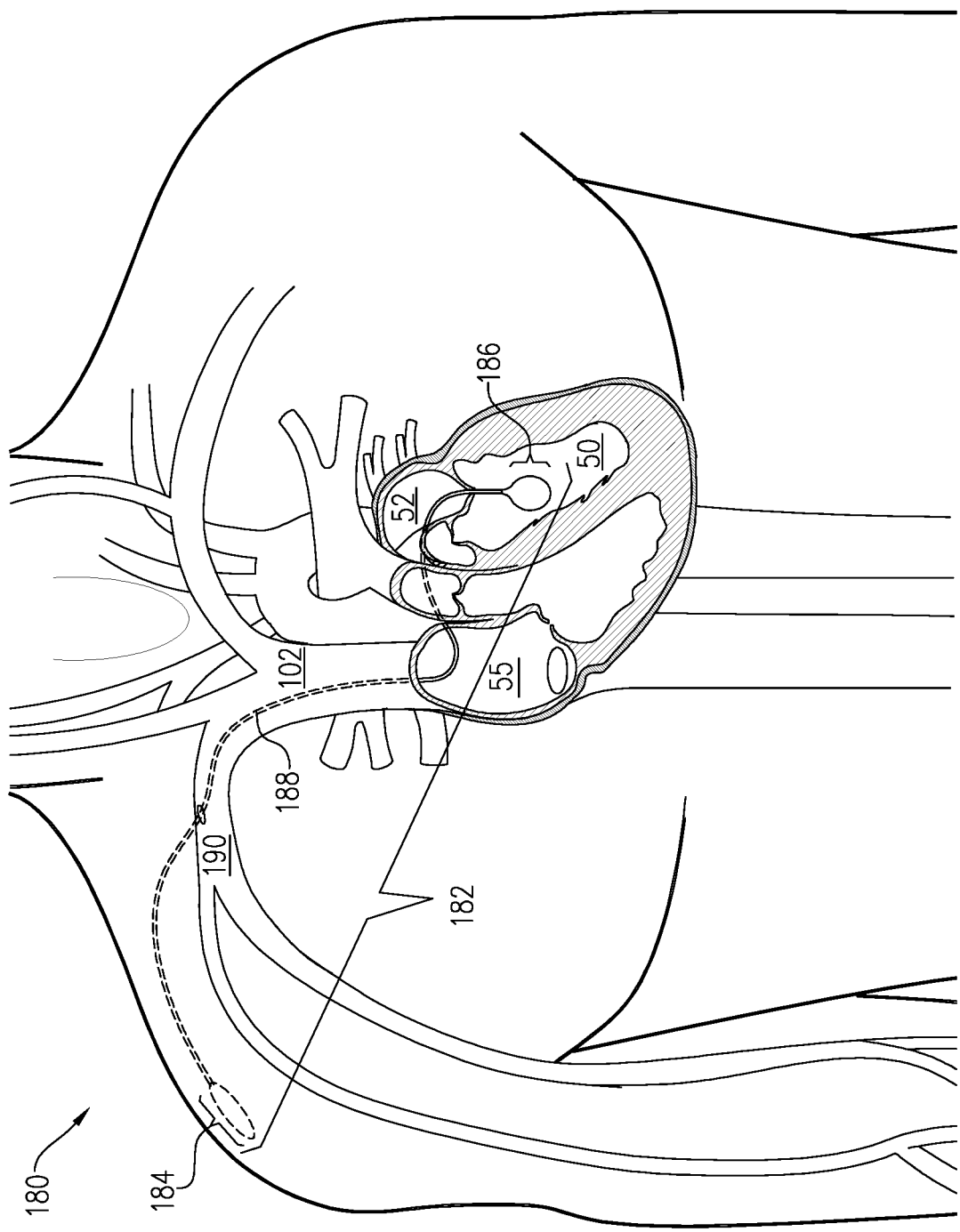
FIG. 11 is a schematic illustration of the operation of a passive pump, in accordance with some applications of the present invention.

Reference is now made to FIG. 11, which is a schematic illustration of a system 180 comprising a passive pump 182 in which a receptacle comprising a bag 186 is positioned within left ventricle 50 and a second receptacle 184 is positioned subcutaneously, in accordance with some applications of the present invention. Receptacle 184 is an extraventricular receptacle. For some applications, a pocket is created subcutaneously for receptacle 184 to be placed within. Typically, a conduit 188 connects bag 186 and receptacle 184. Conduit 188 passes through the mitral valve into left atrium 52, crosses the interatrial septum, e.g., via the fossa ovalis, into right atrium 55, passes through superior vena cava 102 and into a subclavian vein 190. Conduit 188 exits subclavian vein 190 and passes to a subcutaneous location, e.g., near a shoulder, as shown, or any suitable subcutaneous location. Conduit 188 typically comprises a tube having an inner diameter of at least 5 mm in order to allow for passing of fluid between bag 186 and receptacle 184. For some applications of the present invention, passive pump 182 comprises stent structure 30 (described hereinabove with reference to FIGS. 1A-B) surrounding the portion of conduit 188 designated for passing through the interatrial septum or through the fossa ovalis (not shown). For some applications, conduit 188 comprises a tube surrounded by porous material, e.g., a fabric, which facilitates tissue growth around conduit 188 in order to enable sealing of conduit 188 and inhibit leakage of blood out of the vasculature through which conduit passes, e.g., through the interatrial septum or through the passage created in subclavian vein 190. For some applications of the present invention, conduit 188 self-expands to position itself within openings created in the vasculature through which the conduit passes, e.g., through the interatrial septum or through the passage created in subclavian vein 190.

For some applications, bag 186 is similar to or the same as bag 22 described hereinabove with reference to FIGS. 1A-B, 2, 3A-G, 4A-B, 5, and 6A-B. That is, bag 186 is noncompliant.

For some applications, receptacle 184 is similar to or the same as balloon 24 described hereinabove with reference to FIGS. 1A-B, 2, 3A-G, 4A-B, and 5. That is, receptacle 184 is compliant and has wall compliance.

For some applications, receptacle 184 is similar to bag 22 described hereinabove with reference to FIGS. 1A-B, 2, 3A-G, 4A-B, 5, and 6A-B or to bag 84 described hereinabove with reference to FIGS. 6A-B (even without utilizing spring 86). That is, receptacle 184 is noncompliant. In such applications fluid passes from receptacle 184 to bag 186 disposed within left ventricle 50 when pressure in left ventricle 50 reduces from around 120 mmHg to around 5 mmHg Since pressure in the subcutaneous location is higher than 5 mmHg, when pressure in left ventricle 50 drops to around 5 mmHg in Stage B (described hereinabove with reference to FIG. 3B), fluid passes from receptacle 184 at the subcutaneous location, and into bag 186 disposed within left ventricle 50.

Once left ventricle 50 increases in pressure and continues isovolumetric contraction while the mitral and aortic valves remain closed in Stage E (as described hereinabove with reference to FIG. 3E), the increase in pressure in ventricle 50 together with the ventricle having filled with blood pushes the fluid out of bag 186 and through conduit 188 and into receptacle 184 in a manner in which bag 186 is near to empty or empty. Receptacle 184 fills to hold the volume of fluid that was occupying space in ventricle 50 (FIGS. 3B-D) just before the onset of isovolumetric contraction. Moving the volume of fluid out of ventricle 50 produces a corresponding decrease in volume of ventricle 50 during isovolumetric contraction.

Reference is now made to FIGS. 5 and 11. It is to be noted that passive pump 182 may be coupled to a port 64, as described hereinabove with reference to FIG. 5. Port 64 may be directly coupled to receptacle 184. Alternatively, receptacle 184 has a penetrable film and functions as a port.

Reference is now made to FIGS. 3A-G, 4A-B, and 10-11. It is to be noted that passive pump 182 as described with reference to FIG. 11 operates in Stages A-G as described in accordance with the operation of passive pump 21 with reference to FIGS. 3A-G, the graph of FIG. 4A, the table of FIG. 4B, and the pressure/volume graph of FIG. 10, mutatis mutandis.

Reference is now made to FIGS. 6A-B and 11. It is to be noted that system 180 may comprise springs 86 coupled to receptacle 184 as described hereinabove with reference to FIGS. 6A-B. Additionally, fluid is disposed within the internal space and is passable between receptacle 184 and bag 186 via conduit 188. Typically, the internal space contains 10-80 ml of fluid, e.g., 20-40 ml of fluid. Typically, the fluid comprises fluid that is not blood of the patient. For some applications of the present invention, the fluid comprises a gas, such as carbon dioxide, or a liquid, such as saline.

Reference is again made to FIG. 11. Passive pump 182 is implanted using a transcatheter/transvascular approach and advantageously does not require making an incision in myocardial tissue of the heart of the patient.

Reference is now made to FIGS. 12A-B, which are schematic illustrations of a system 200 comprising a passive pump 202 comprising two bags 22 and 204 and an energy-storage element 250 comprising a plurality of struts 206, in accordance with some applications of the present invention. Bag 204 typically functions as an extraventricular receptacle. It is to be noted that system 200 is similar to system 20 described hereinabove with reference to FIG. 1A, like reference numbers referring to like parts, with the exception that passive pump 202 does not comprise compliant balloon 24. Bags 22 and 204 have similar wall compliance (for example, effectively no compliance at pressures less than 120 mmHg). For some applications, each of bags 22 and 204 has, in the absence of any external forces applied thereto: (a) a first volume when bags 22 and 204 each has an internal pressure of 120 mmHg, and (b) a second volume when the bags 22 and 204 each has an internal pressure of 10 mmHg, the first volume being less than 110% of the second volume.

Fluid is disposed within the internal space and is passable between bags 22 and 204 via conduit 26. Typically, the internal space contains 10-80 ml of fluid, e.g., 20-40 ml of fluid. Typically, the fluid comprises fluid that is not blood of the patient. For some applications of the present invention, the fluid comprises a gas, such as carbon dioxide, or a liquid, such as saline.

It is to be noted that bag 204 has little to no wall compliance, however, the presence of stent structure 250a imparts compliance to the section of passive pump 202 that comprises bag 204 and energy-storage element 250.

For some applications, similarly as shown in FIGS. 2, 3A-G, 5, 8, 9, and 11, bag 204 may be positioned outside of the heart and function as an extracardiac receptacle. For some applications in which bag 204 is an extracardiac receptacle, conduit 26 passes through myocardium and functions as a transmyocardial conduit.

Energy-storage element 250 comprises a stent structure 250a comprising a plurality of struts 206 surrounding bag 204. Typically, struts 206 comprise a flexible material, e.g., nitinol. A respective portion 230 of each of struts 206 is configured to (1) assume a longitudinally-elongated state upon the filling of the expandable extraventricular receptacle (e.g., bag 204) from the first state to the second, expanded state (FIG. 12A), (2) assume an energy-released, longitudinally-shortened state (FIG. 12B), and (3) return the expandable extraventricular receptacle (e.g., bag 204) from the second, expanded state to the first state during a transition of energy-storage element 250 (e.g., struts 206) from the longitudinally-elongated state toward the longitudinally-shortened state. In the longitudinally-shortened state of portions 230 of struts 206 shown in FIG. 12B, portions 230 of struts 206 are each typically shaped so as to define a bend which projects laterally away from a central longitudinal axis ax1 of pump 202. In such a manner, portions 230 expand radially and shorten longitudinally with respect to axis ax1. It is to be noted that the first state and the second expanded state of bag 204 (i.e., the expandable extraventricular receptacle) and the respective states of intraventricular bag 22 shown in FIGS. 12A-B are not drawn to scale.

Each strut 206 extends longitudinally along an external surface of the extraventricular receptable (e.g., bag 204) in a direction (1) from a portion 240 of the extraventricular receptable (e.g., bag 204) that is furthest from the intraventricular receptable (e.g., bag 22), and toward (2) the intraventricular receptable (e.g., bag 22). Pump 202 comprises stent structure 30 which has a first portion that surrounds conduit 26. Energy-storage element 250 defines a second portion of stent structure 30 that surrounds the extraventricular receptacle (e.g., bag 204). A part of the first portion of stent structure 30 (i.e., a wider portion 212) surrounds a portion of the intraventricular receptacle (e.g., bag 22). Stent structure 30 is (i) compressed during delivery of pump 202 into the body of the patient, and (ii) expandable during implantation of pump 202 in the body of the patient. Once expanded, first portion 210 of stent structure 30 is shaped so as to define (1) a narrowed portion 210 at conduit 26 and (2) wider portion 212 than narrowed portion 210, at the part of the first portion of the stent structure that surrounds the portion of the intraventricular receptacle (e.g., bag 22).

Stent structure 250a has a longitudinally-shortened state (FIG. 12B) and an energy-storage state (FIG. 12A) upon bag 204 assuming a greater volume. Once the pressure in the ventricle decreases during diastole, stent structure 250a releases the energy stored in it, expelling the fluid from within bag 204 into bag 22. That is, stent structure 250a is configured to (1) absorb energy upon filling of bag 204 (i.e., the extraventricular receptacle) from a first state to a second, expanded state, and (2) release the energy to return bag 204 (i.e., the extraventricular receptacle) from the second, expanded state to the first state.

Reference is now made to FIGS. 3A-G, 4A-B, 10, and 12A-B. It is to be noted that passive pump 202 as described with reference to FIGS. 12A-B operates in Stages A-G as described in accordance with the operation of passive pump 21 with reference to FIGS. 3A-G, the graph of FIG. 4A, the table of FIG. 4B, and the pressure/volume graph of FIG. 10, mutatis mutandis.

Figure 13B:
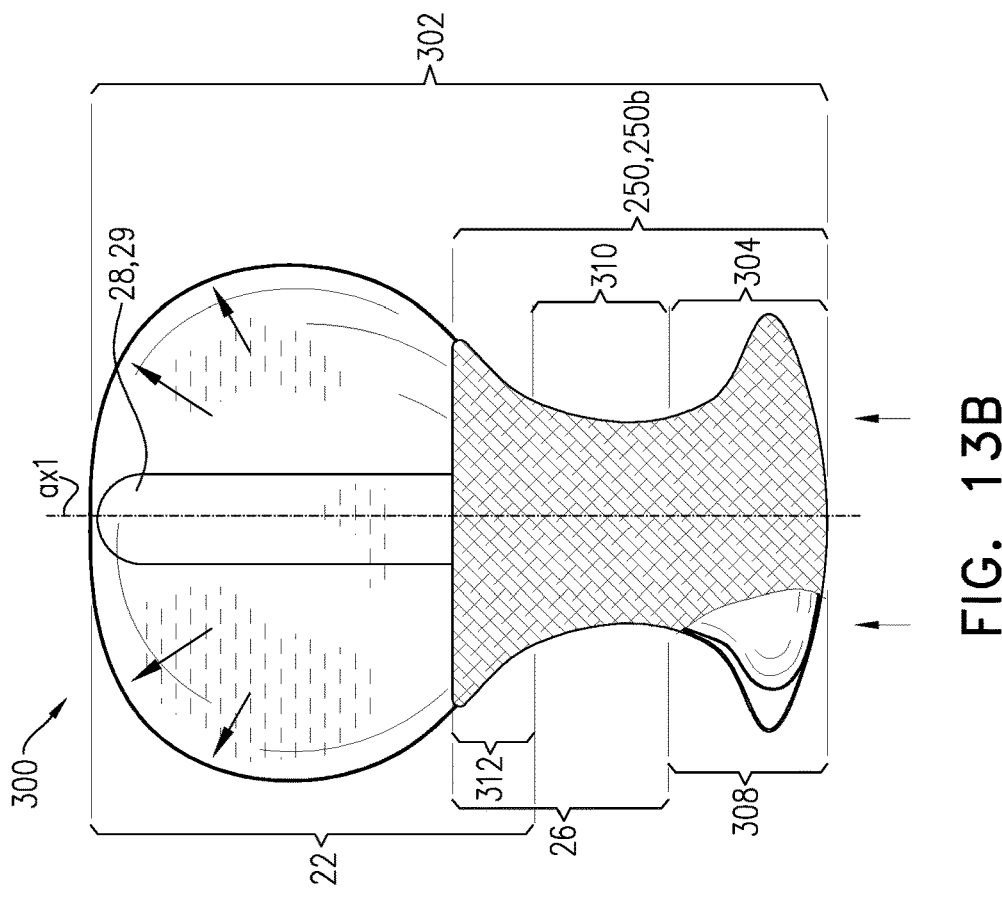
FIGS. 13A-B are schematic illustrations of a passive pump comprising two noncompliant bags and braided mesh, in accordance with some applications of the present invention.
Figure 13A:
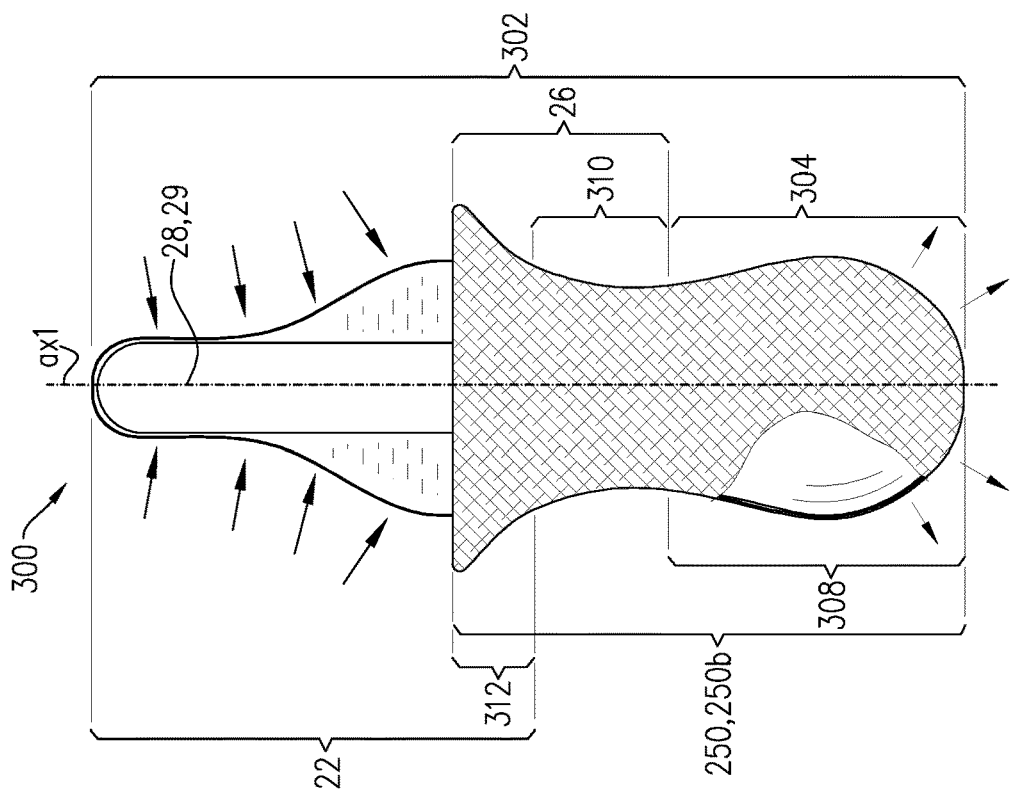

Reference is now made to FIGS. 13A-B, which are schematic illustrations of a system 300 comprising a passive pump 302 comprising two bags 22 and 304 and an energy-storage element 250 comprising a mesh 250b, in accordance with some applications of the present invention. Bag 304 typically functions as an extraventricular receptacle. It is to be noted that system 300 is similar to system 20 described hereinabove with reference to FIG. 1A, like reference numbers referring to like parts, with the exception that passive pump 302 does not comprise compliant balloon 24. Bags 22 and 304 have similar wall compliance (for example, effectively no compliance at pressures less than 120 mmHg). For some applications, each of bags 22 and 304 has, in the absence of any external forces applied thereto: (a) a first volume when bags 22 and 304 each has an internal pressure of 120 mmHg, and (b) a second volume when the bags 22 and 304 each has an internal pressure of 10 mmHg, the first volume being less than 110% of the second volume.

Fluid is disposed within the internal space and is passable between bags 22 and 304 via conduit 26. Typically, the internal space contains 10-80 ml of fluid, e.g., 20-40 ml of fluid. Typically, the fluid comprises fluid that is not blood of the patient. For some applications of the present invention, the fluid comprises a gas, such as carbon dioxide, or a liquid, such as saline.

It is to be noted that bag 304 has little to no wall compliance, however, the presence of mesh 250b imparts compliance to the section of passive pump 302 that comprises bag 304 and energy-storage element 250.

For some applications, similarly as shown in FIGS. 2, 3A-G, 5, 8, 9, and 11, bag 304 may be positioned outside of the heart and function as an extracardiac receptacle. For some applications in which bag 304 is an extracardiac receptacle, conduit 26 passes through myocardium and functions as a transmyocardial conduit.

Energy-storage element 250 comprises mesh 250b surrounding bag 204 and conduit 26. Typically, mesh 250b comprises nitinol or stainless steel. A first portion 308 of mesh 250b is configured to (1) assume a longitudinally-elongated state upon the filling of the expandable extraventricular receptacle (e.g., bag 304) from the first state to the second, expanded state (FIG. 13A), (2) assume an energy-released, longitudinally-shortened state (FIG. 13B), and (3) return the expandable extraventricular receptacle (e.g., bag 304) from the second, expanded state to the first state during a transition of energy-storage element 250 (e.g., mesh 250b) from the longitudinally-elongated state toward the longitudinally-shortened state. As portion 308 of mesh 250b releases the energy, portion 308 of mesh 250b transitions toward an energy-released state in which first portion 308 of mesh 250b expands radially and shortens longitudinally, with respect to a central longitudinal axis ax1 of the pump 302.

Mesh 250b is (i) compressed during delivery of pump 302 into the body of the patient, and (ii) expandable during implantation of pump 302 in the body of the patient. Once expanded from the delivery state, mesh 250b is shaped so as to define a second, narrowed portion 310 of mesh 250b that surrounds conduit 26, and a third, wider (typically flared) portion 312 of mesh 250b surrounds a portion of the intraventricular receptacle (i.e., bag 22). Wider portion 312 is typically wider than second, narrowed portion 310.

Mesh 250b has a longitudinally-shortened state (FIG. 13B) and an energy-storage state (FIG. 13A) upon bag 304 assuming a greater volume. Once the pressure in the ventricle decreases during diastole, portion 308 of mesh 250b releases the energy stored in it, expelling the fluid from within bag 304 into bag 22. That is, portion 308 of mesh 250b is configured to (1) absorb energy upon filling of bag 304 (i.e., the extraventricular receptacle) from a first state to a second, expanded state, and (2) release the energy to return bag 304 (i.e., the extraventricular receptacle) from the second, expanded state to the first state. It is to be noted that the first state and the second expanded state of bag 304 (i.e., the expandable extraventricular receptacle) and the respective states of intraventricular bag 22 shown in FIGS. 13A-B are not drawn to scale.

It is to be noted that pump 302 is shown as having mesh 250b surround a portion of bag 22, conduit 26, and bag 304. It is to be noted that pump 302 may comprise mesh 250b surrounding bag 304, while the portion of bag 22 and conduit 26 may be surrounded by stent structure 30, as described hereinabove with reference to FIGS. 1A-B, for example.

Reference is now made to FIGS. 3A-G, 4A-B, 10, and 13A-B. It is to be noted that passive pump 302 as described with reference to FIGS. 13A-B operates in Stages A-G as described in accordance with the operation of passive pump 21 with reference to FIGS. 3A-G, the graph of FIG. 4A, the table of FIG. 4B, and the pressure/volume graph of FIG. 10, mutatis mutandis.

Figure 14B:
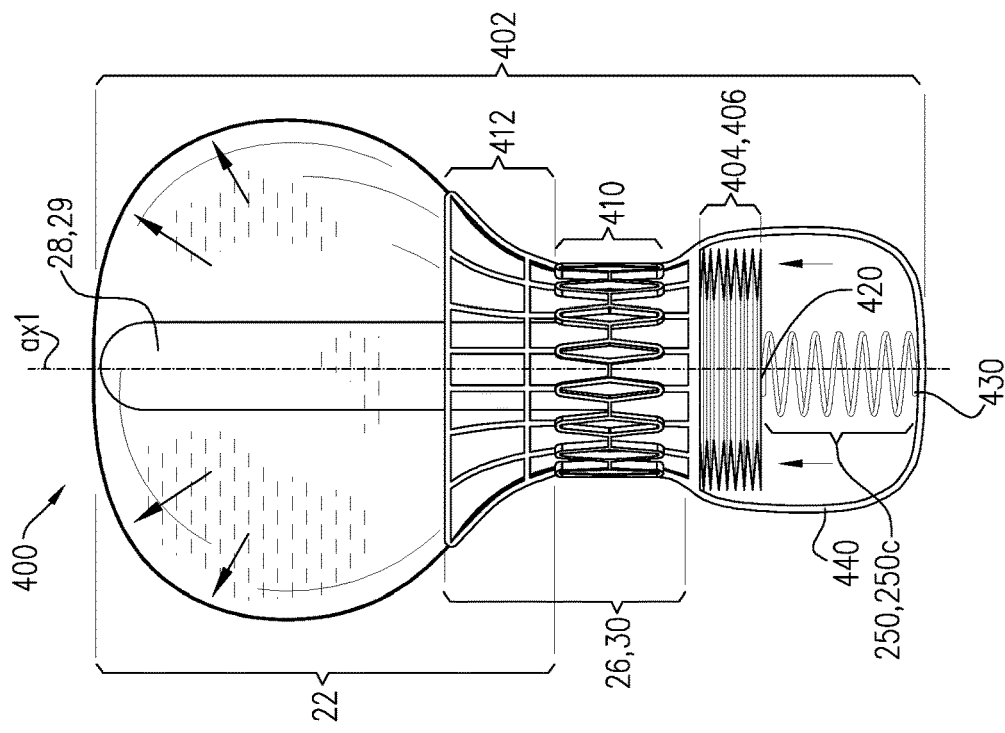
FIGS. 14A-B are schematic illustrations of a passive pump comprising two noncompliant bags and bellows coupled to a spring, in accordance with some applications of the present invention.
Figure 14A:
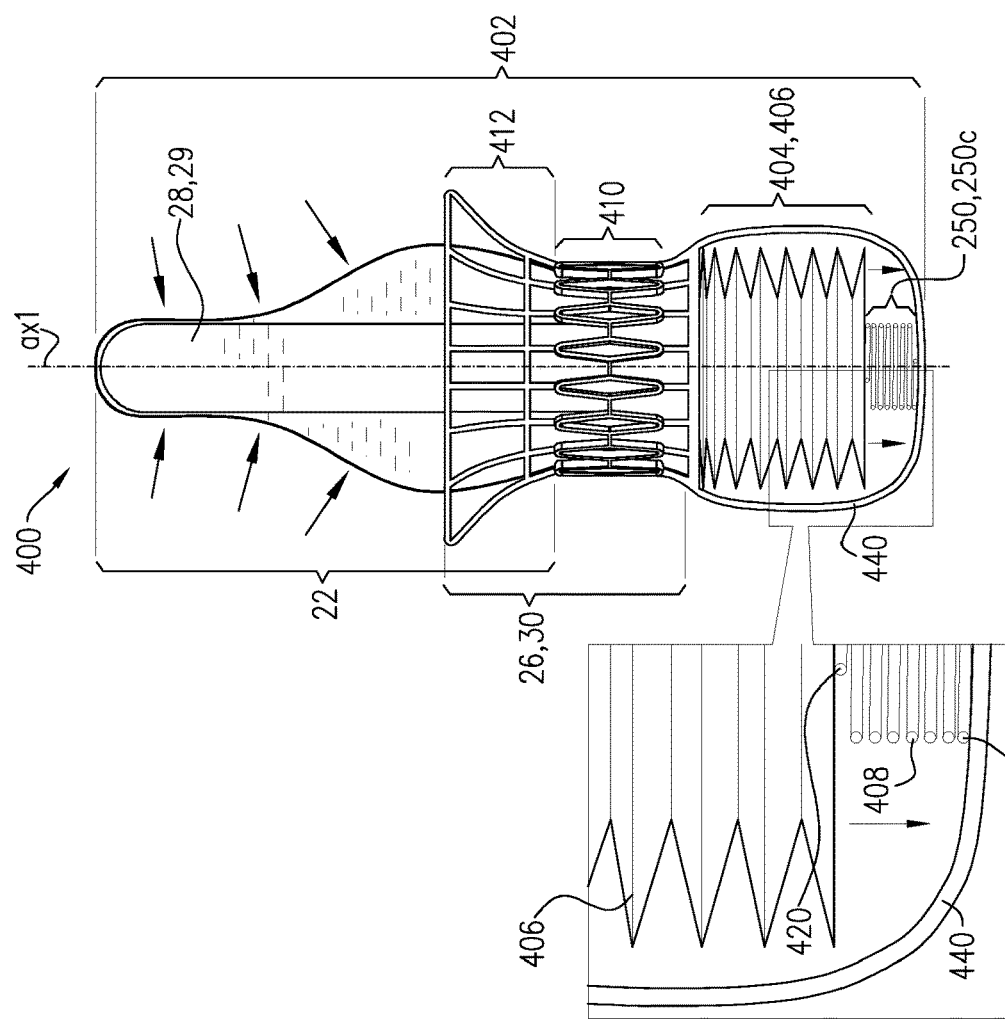

Reference is now made to FIGS. 14A-B, which are schematic illustrations of a system 400 comprising a passive pump 402 comprising bag 22, an extraventricular receptacle 404 comprising a bellows 406, and an energy-storage element 250 comprising a coil spring 250c, in accordance with some applications of the present invention. It is to be noted that system 400 is similar to system 20 described hereinabove with reference to FIG. 1A, like reference numbers referring to like parts, with the exception that passive pump 402 does not comprise compliant balloon 24. Bag 22 and bellows 406 has similar wall compliance (for example, effectively no compliance at pressures less than 120 mmHg). For some applications, each of bag 22 and bellows 406 have, in the absence of any external forces applied thereto: (a) a first volume when bag 22 and bellows 406 each has an internal pressure of 120 mmHg, and (b) a second volume when the bag 22 and bellows 406 each has an internal pressure of 10 mmHg, the first volume being less than 110% of the second volume.

Bellows 406 is typically disposed between bag 22 (i.e., the intraventricular receptacle) and energy-storage element 250.

Fluid is disposed within the internal space and is passable between bag 22 and bellows 406 via conduit 26. Typically, the internal space contains 10-80 ml of fluid, e.g., 20-40 ml of fluid. Typically, the fluid comprises fluid that is not blood of the patient. For some applications of the present invention, the fluid comprises a gas, such as carbon dioxide, or a liquid, such as saline.

It is to be noted that bellows 406 has little to no wall compliance, however, the presence of spring 250c imparts compliance to the section of passive pump 402 that comprises bellows 406.

For some applications, similarly as shown in FIGS. 2, 3A-G, 5, 8, 9, and 11, bellows 406 may be positioned outside of the heart and function as an extracardiac receptacle. For some applications in which bellows 406 is an extracardiac receptacle, conduit 26 passes through myocardium and functions as a transmyocardial conduit.

Typically, energy-storage element 250 comprises coil spring 250c comprising a shape-memory material, e.g., nitinol. Energy-storage element 250 comprises coil spring 250c that is configured to (1) assume a compressed, longitudinally-shortened, state upon the filling of the expandable extraventricular receptacle (e.g., bellows 406) from a first state to a second, expanded state (FIG. 14A), and (2) return the expandable extraventricular receptacle (e.g., bellows 406) from the second, expanded state to the first state (FIG. 14B) during a transition of energy-storage element 250 (e.g., coil spring 250c) from the compressed, longitudinally-shortened state toward an energy-released state of spring 250c. As coil spring 250c releases the energy, coil spring 250c lengthens longitudinally, with respect to a central longitudinal axis ax1 of pump 402.

Bellows 406 and coil spring 250c are surrounded by scaffolding 440, e.g., a frame or a housing. Energy-storage element 250 is coupled at a first end 420 of energy-storage element 250 to an outer surface of bellows 406, and at a second end 430 of energy-storage element 250 to a portion of scaffolding 440. During the absorbing and releasing of energy by energy-storage element 250, first end 420 of energy-storage element 250 moves, respectively, toward and away from second end 430 of energy-storage element 250. For some applications, scaffolding 440 is coupled to stent structure 30 that surrounds conduit 26 and a portion of bag 22, as described hereinabove with reference to FIGS. 1A-B, for example. For some applications, scaffolding 440 is part of stent structure 30. Scaffolding 440 and stent structure 30 are (i) compressed during delivery of pump 402 into the body of the patient, and (ii) expandable during implantation of pump 402 in the body of the patient.

Coil spring 250c has an energy-storage state (FIG. 14A) upon bellows 406 assuming a greater volume, and an energy-released state (FIG. 14B). Once the pressure in the ventricle decreases during diastole, coil spring 250c releases the energy stored in it, expelling the fluid from within bellows 406 into bag 22. That is, coil spring 250c is configured to (1) absorb energy upon filling of bellows 406 (i.e., the extraventricular receptacle) from a first state to a second, expanded state, and (2) release the energy to return bellows 406 (i.e., the extraventricular receptacle) from the second, expanded state to the first state. It is to be noted that the first state and the second expanded state of bellows 406 (i.e., the expandable extraventricular receptacle) and the respective states of intraventricular bag 22 shown in FIGS. 14A-B are not drawn to scale.

Reference is now made to FIGS. 3A-G, 4A-B, 10, and 14A-B. It is to be noted that passive pump 402 as described with reference to FIGS. 14A-B operates in Stages A-G as described in accordance with the operation of passive pump 21 with reference to FIGS. 3A-G, the graph of FIG. 4A, the table of FIG. 4B, and the pressure/volume graph of FIG. 10, mutatis mutandis.

Reference is now made to FIGS. 15A-B, which are schematic illustrations of a system 500 comprising a passive pump 502 comprising bag 22, an extraventricular receptacle 504 comprising a bellows 506, and an energy-storage element 250 comprising a coil spring 250d, in accordance with some applications of the present invention. It is to be noted that system 500 is similar to system 20 described hereinabove with reference to FIG. 1A, like reference numbers referring to like parts, with the exception that passive pump 502 does not comprise compliant balloon 24. Bag 22 and bellows 506 have similar wall compliance (for example, effectively no compliance at pressures less than 120 mmHg). For some applications, each of bag 22 and bellows 506 has, in the absence of any external forces applied thereto: (a) a first volume when bag 22 and bellows 506 each has an internal pressure of 120 mmHg, and (b) a second volume when the bag 22 and bellows 506 each has an internal pressure of 10 mmHg, the first volume being less than 110% of the second volume.

Typically, energy-storage element 250 comprises coil spring 250*d* comprising a shape-memory material, e.g., nitinol.

Coil spring 250*d* surrounds bellows 506 at least in part. Coil spring 250*d* wraps around bellows 506 between folds 507 of bellows 506.

Fluid is disposed within the internal space and is passable between bag 22 and bellows 506 via conduit 26. Typically, the internal space contains 10-80 ml of fluid, e.g., 20-40 ml of fluid. Typically, the fluid comprises fluid that is not blood of the patient. For some applications of the present invention, the fluid comprises a gas, such as carbon dioxide, or a liquid, such as saline.

It is to be noted that bellows 506 has little to no wall compliance, however, the presence of spring 250*d* imparts compliance to the section of passive pump 502 that comprises bellows 506.

For some applications, similarly as shown in FIGS. 2, 3A-G, 5, 8, 9, and 11, bellows 506 may be positioned outside of the heart and function as an extracardiac receptacle. For some applications in which bellows 506 is an extracardiac receptacle, conduit 26 passes through myocardium and functions as a transmyocardial conduit.

Energy-storage element 250 comprises coil spring 250*d* that comprises a shape-memory material that is configured to (1) assume a longitudinally-elongated state upon the filling of the expandable extraventricular receptacle (e.g., bellows 506) from a first state to a second, expanded state (FIG. 15A), and (2) return the expandable extraventricular receptacle (e.g., bellows 506) from the second, expanded state to the first state (FIG. 15B) during a transition of energy-storage element 250 (e.g., coil spring 250*d*) from the longitudinally-elongated state toward an energy-released state of coil spring 250*d*. As coil spring 250*d* releases the energy, coil spring 250*d* transitions toward the energy-released state in which coil spring 250*d* shortens longitudinally, with respect to a central longitudinal axis ax1 of pump 502.

Bellows 506 and coil spring 250*d* are surrounded by scaffolding 540, e.g., a frame or a housing. For some applications, scaffolding 540 is coupled to stent structure 30 that surrounds conduit 26 and a portion of bag 22, as described hereinabove with reference to FIGS. 1A-B, for example. For some applications, scaffolding 540 is part of stent structure 30. Scaffolding 540 and stent structure 30 are (i) compressed during delivery of pump 502 into the body of the patient, and (ii) expandable during implantation of pump 502 in the body of the patient.

Coil spring 250*d* has an energy-storage state (FIG. 15A) upon bellows 506 assuming a greater volume, and an energy-released state (FIG. 15B). Once the pressure in the ventricle decreases during diastole, coil spring 250*d* releases the energy stored in it, expelling the fluid from within bellows 506 into bag 22. That is, coil spring 250*d* is configured to (1) absorb energy upon filling of bellows 506 (i.e., the extraventricular receptacle) from a first state to a second, expanded state, and (2) release the energy to return bellows 506 (i.e., the extraventricular receptacle) from the second, expanded state to the first state. It is to be noted that the first state and the second expanded state of bellows 506 (i.e., the expandable extraventricular receptacle) and the respective states of intraventricular bag 22 shown in FIGS. 15A-B are not drawn to scale.

Reference is now made to FIGS. 3A-G, 4A-B, 10, and 15A-B. It is to be noted that passive pump 502 as described with reference to FIGS. 15A-B operates in Stages A-G as described in accordance with the operation of passive pump 21 with reference to FIGS. 3A-G, the graph of FIG. 4A, the table of FIG. 4B, and the pressure/volume graph of FIG. 10, mutatis mutandis.

Reference is now made to FIGS. 1A-15B. It is to be noted that although systems described herein are applied to assist and repair a failing left ventricle 50 of the heart of the patient, the systems described herein can also be applied to assist and repair a failing right ventricle, mutatis mutandis. It is to be noted that bags 22, 84, 96, and 186; receptacles 94 and 184; balloon 24; and bellows 406 and 506 may comprise a polymer (e.g., polyurethane or any other suitable elastic material), which is configured to retain elasticity for an extended period of time.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for repairing a heart, comprising:
   identifying a heart of a patient as having a reduced ejection fraction; and
   in response to the identifying, reducing wall stress of a ventricle of the heart by implanting apparatus that facilitates cyclical moving of fluid that is not blood of the patient into and out of the ventricle of the heart, the moving comprising:
   during ventricular diastole, moving a volume of the fluid into the ventricle in a manner that produces a corresponding decrease in a total volume of blood that fills the ventricle during diastole; and
   during ventricular systole, moving the volume of the fluid out of the ventricle in a manner that produces a corresponding decrease in a total volume of the ventricle during isovolumetric contraction of the ventricle.

2. The method according to claim 1, wherein implanting the apparatus comprises reducing a volume of blood expelled by the ventricle during systole.

3. The method according to claim 1, wherein moving the volume of the fluid out of the ventricle comprises moving the volume of the fluid out of the heart.

4. The method according to claim 1, wherein implanting the apparatus comprises implanting apparatus including a bag, a compliant balloon and a conduit disposed between and in fluid communication with the bag and the compliant balloon, in a manner in which (1) the bag is disposed within the ventricle, and (2) the compliant balloon is disposed outside the ventricle.

5. The method according to claim 4, wherein wall compliance of the balloon is at least three times wall compliance of the bag.

6. The method according to claim 4, wherein the bag is noncompliant.

7. The method according to claim 4, wherein implanting the apparatus comprises positioning the bag in a left ventricle.

8. The method according to claim 4, wherein implanting the apparatus comprises positioning the bag in a right ventricle.

9. The method according to claim 4, wherein implanting the apparatus comprises:
   positioning the balloon at an extracardiac space, and
   positioning the conduit transmyocardially.

10. The method according to claim 4, wherein implanting the apparatus comprises (1) positioning the balloon in a right atrium, and (2) positioning the bag in a left ventricle, and wherein the method further comprises implanting the apparatus in a manner in which the conduit extends from the left ventricle to the right atrium.

11. The method according to claim 1, wherein implanting apparatus comprises implanting apparatus including a first bag, a second bag and a conduit disposed between and in fluid communication with the first bag and the second bag, in a manner in which (1) the first bag is disposed within the ventricle, and (2) the second bag is disposed outside the ventricle.

12. The method according to claim 11, wherein the first and second bags are noncompliant.

13. The method according to claim 11, wherein implanting the apparatus comprises positioning the first bag in a left ventricle.

14. The method according to claim 11, wherein implanting the apparatus comprises positioning the first bag in a right ventricle.

15. The method according to claim 11, wherein implanting the apparatus comprises:
positioning the second bag at an extracardiac space, and
positioning the conduit transmyocardially.

16. The method according to claim 11, wherein implanting the apparatus comprises positioning (1) the first bag in a left ventricle, and (2) the second bag in a right atrium, and wherein the method further comprises implanting the apparatus in a manner in which the conduit extends from the left ventricle to the right atrium.

17. The method according to claim 11, wherein implanting the apparatus comprises positioning (1) the first bag in a left ventricle, and (2) the second bag in a superior vena cava, and wherein the method further comprises implanting the apparatus in a manner in which the conduit extends from the left ventricle to the superior vena cava.

18. The method according to claim 11, wherein implanting the apparatus comprises positioning (1) the first bag in a left ventricle, and (2) the second bag in an inferior vena cava, and wherein the method further comprises implanting the apparatus in a manner in which the conduit extends from the left ventricle to the inferior vena cava.

19. The method according to claim 11, wherein the apparatus comprises an energy-storage element coupled to the second bag and configured to:

absorb energy upon filling of the second bag from a first state to a second, expanded state, and
release the energy to return the second bag from the second, expanded state to the first state.

20. The method according to claim 19, wherein the energy-storage element comprises a plurality of struts surrounding the second bag, wherein a respective portion of each of the struts is configured to:
assume a longitudinally-elongated state upon the filling of the second bag from the first state to the second, expanded state,
assume a longitudinally-shortened state, and
return the second bag from the second, expanded state to the first state during a transition of the energy-storage element from the longitudinally-elongated state toward the longitudinally-shortened state.

21. The method according to claim 19, wherein the energy-storage element comprises a mesh having a first portion surrounding the second bag, wherein the first portion of the mesh is configured to:
absorb the energy upon the filling of the second bag from the first state to the second, expanded state, and
release the energy to return the second bag from the second, expanded state to the first state.

22. The method according to claim 19, wherein the second bag comprises a bellows, and wherein the energy-storage element is coupled to the bellows.

23. The method according to claim 1, wherein implanting the apparatus comprises acutely further reducing the ejection fraction and chronically increasing the ejection fraction.

24. The method according to claim 4, wherein implanting the apparatus comprises (1) positioning the balloon in a superior vena cava, and (2) positioning the bag in a left ventricle, and wherein the method further comprises implanting the apparatus in a manner in which the conduit extends from the left ventricle to the superior vena cava.

25. The method according to claim 4, wherein implanting the apparatus comprises (1) positioning the balloon in an inferior vena cava, and (2) positioning the bag in a left ventricle, and wherein the method further comprises implanting the apparatus in a manner in which the conduit extends from the left ventricle to the inferior vena cava.

* * * * *